(12) United States Patent
Stanley, Sr. et al.

(10) Patent No.: US 11,351,191 B2
(45) Date of Patent: Jun. 7, 2022

(54) SILICATE CONTAINING COMPOSITIONS AND METHODS OF TREATMENT

(71) Applicant: HS PHARMACEUTICALS, LLC, Greenville, SC (US)

(72) Inventors: Richard Thomas Stanley, Sr., Easley, SC (US); David Edward Stanley, Easley, SC (US); Marcus Blackstone, Gray Court, SC (US); Thomas Wagner, Greer, SC (US)

(73) Assignee: HS PHARMACEUTICALS, LLC, Greenville, SC (US)

( * ) Notice: Subject to any disclaimer, the term of this patent is extended or adjusted under 35 U.S.C. 154(b) by 0 days.

(21) Appl. No.: 16/670,060

(22) Filed: Oct. 31, 2019

(65) Prior Publication Data

US 2020/0061104 A1 Feb. 27, 2020

Related U.S. Application Data

(63) Continuation of application No. 15/856,598, filed on Dec. 28, 2017, now Pat. No. 10,493,097, which is a continuation of application No. 12/250,624, filed on Oct. 14, 2008, now Pat. No. 9,889,151.

(60) Provisional application No. 61/090,833, filed on Aug. 21, 2008, provisional application No. 61/071,754, filed on May 15, 2008, provisional application No. 60/960,794, filed on Oct. 15, 2007.

(51) Int. Cl.
| | |
|---|---|
| *A61K 33/00* | (2006.01) |
| *A61K 31/70* | (2006.01) |
| *A61P 31/00* | (2006.01) |
| *A61P 31/04* | (2006.01) |
| *A61P 31/18* | (2006.01) |
| *A61P 43/00* | (2006.01) |
| *A61P 31/22* | (2006.01) |

(52) U.S. Cl.
CPC .............. *A61K 33/00* (2013.01); *A61K 31/70* (2013.01); *A61P 31/00* (2018.01); *A61P 31/04* (2018.01); *A61P 31/18* (2018.01); *A61P 31/22* (2018.01); *A61P 43/00* (2018.01); *Y02A 50/30* (2018.01)

(58) Field of Classification Search
None
See application file for complete search history.

(56) References Cited

U.S. PATENT DOCUMENTS

| | | | |
|---|---|---|---|
| 1,688,228 A | 10/1928 | Busch | |
| 4,029,770 A | 6/1977 | Willard, Sr. | |
| 4,563,351 A | 1/1986 | Caslavsky et al. | |
| 5,080,900 A | 1/1992 | Stanley | |
| 5,370,876 A | 12/1994 | Noll et al. | |
| 5,534,509 A | 7/1996 | Konishi et al. | |
| 5,658,896 A | 8/1997 | Konishi et al. | |
| 5,807,951 A | 9/1998 | Konishi et al. | |
| 5,922,360 A | 7/1999 | Bronder | |
| 6,149,947 A | 11/2000 | Hon et al. | |
| 6,214,391 B1 | 4/2001 | Ju et al. | |
| 6,288,045 B1 | 9/2001 | Kaufman | |
| 6,335,457 B1 | 1/2002 | Seguin | |
| 6,692,775 B2 | 2/2004 | Young | |
| 6,884,440 B2 | 4/2005 | Choi et al. | |
| 7,014,870 B1 | 3/2006 | Hon et al. | |
| 7,915,198 B2 | 3/2011 | Kros | |
| 8,187,473 B2 | 5/2012 | Prasad | |
| 9,333,224 B2 | 5/2016 | Stanley et al. | |
| 9,889,151 B2 | 2/2018 | Stanley et al. | |
| 2003/0185900 A1 | 10/2003 | Choi et al. | |
| 2004/0057958 A1 | 3/2004 | Waggoner, Jr. et al. | |
| 2004/0097467 A1 | 5/2004 | Juturu et al. | |
| 2006/0161089 A1 | 7/2006 | Thierauf et al. | |
| 2006/0178268 A1* | 8/2006 | Kros ........................ C05G 5/27 504/101 |
| 2006/0246154 A1 | 11/2006 | Hon et al. | |
| 2009/0130230 A1 | 5/2009 | Stanley, Sr. et al. | |
| 2010/0278935 A1 | 11/2010 | Stacey | |
| 2011/0229577 A1 | 9/2011 | Kerek | |
| 2013/0130902 A1 | 5/2013 | Roose et al. | |
| 2013/0149396 A1 | 6/2013 | Stanley et al. | |
| 2017/0042934 A1 | 2/2017 | Bastos et al. | |
| 2018/0221405 A1 | 8/2018 | Stanley et al. | |

FOREIGN PATENT DOCUMENTS

| | | |
|---|---|---|
| CA | 2 298 762 A1 | 12/2000 |
| CN | 1 634 127 A | 7/2005 |
| RU | 2 182 006 C2 | 5/2002 |

(Continued)

OTHER PUBLICATIONS

Adenis A, Ray-Coquard I, Italiano A, Chauzit E, Bui-Nguyen B, Blay JY, Tresch-Bruneel E, Fournier C, Clisant S, Amela EY, Gassier PA, Molimard M & Penel N. A dose-escalating phase I of imatinib mesylate with fixed dose of metronomic cyclophosphamide in targeted solid tumours. Br J Cancer 2013; 109:2574-8.

Ahmad et al., "Apoptosis induction by silica nanoparticles mediated through reactive oxygen species in human liver cell line HepG2," Toxicol. Appl. Pharmacol. 259:160-168 (2012).

Akhtar et al., "Nanotoxicity of pure silica mediated through oxidant generation rather than glutathione depletion in human lung epithelial cells," Toxicology 276:95-102 (2010).

Al-Rawi et al., "Uptake and intracellular localization of submicron and nano-sized SiO2 particles in HeLa cells," Arch. Toxicol 85:813-826 (2011).

(Continued)

*Primary Examiner* — Susan T Tran
(74) *Attorney, Agent, or Firm* — Cooley LLP

(57) ABSTRACT

The present invention relates to compositions comprising a silicate and methods of use thereof. In particular, the compositions of the present invention are suitable for treating inflammatory conditions, cancer, bacterial and viral infections, and infected and uninfected wounds. The compositions of the present invention can also be useful in treating spinal cord injury, tissue remodeling, and promoting bone growth and repair.

19 Claims, 8 Drawing Sheets

(56) References Cited

FOREIGN PATENT DOCUMENTS

| RU | 2 237 483 C1 | 10/2004 |
|---|---|---|
| RU | 2 280 458 C1 | 7/2006 |
| WO | WO 2006/136003 A1 | 12/2006 |
| WO | WO 2008/147468 A2 | 12/2008 |
| WO | WO 2009/018356 A1 | 2/2009 |
| WO | WO 2009/052090 A2 | 4/2009 |

OTHER PUBLICATIONS

Alvarez et al., "A Randomized Double Blind Study to Evaluate the Effect of an Oak Bark Extract in Two Different Topical Preparations on the Healing of Partial Thickness Wounds in Healthy Human Volunteers," 18 pages, Study at University Wound Healing Clinic (1991).
Annex to Form PCT/ISA/206—Communication Relating to the Results of the Partial International Search Report for related International Patent Application No. PCT/US2008/079802, completed Jul. 20, 2009. Cannot Locate.
Araki et al., "Spectroscopic analysis of tissues (12). On the quantitative analysis of silicon in tumor tissue,"Jpn. J. Canc. Res. 41:187-189 (1951).
Arslan C & Yalcin S. Current and future systemic treatment options in metastatic pancreatic cancer. J Gastrointest Oncol 2014; 5:280-95.
Aubert and Cannell, "Restructuring of Colloidal Silica Aggregates," Phys. Rev. Lett. 56(7):738-741 (1986).
Aveston, "Hydrolysis of Sodium Silicate: Ultracetrifugation in Chloride Solutions," J. Chem. Soc. 4444-4448 (1965).
Bagwe et al., "Surface Modification of Silica Nanoparticles to Reduce Aggregation and Nonspecific Binding," Langmuir 22:4357-4362 (2006).
Barandeh et al., "Organically Modified Silica Nanoparticles Are Biocompatible and Can Be Targeted to Neurons In Vivo," PLOS One 7(1):e29424 (2012).
Battye, "Upon the Medicinal Properties of Silica in Cancer, Fibroid Tumours, and Diabetes," Edinburgh Medical Journal 20:420-435 (1874).
Bauer et al., "Cytotoxicity of silica nanoparticles through exocytosis of von Willebrand factor and necrotic cell death in primary human endothelial cells," Biomaterials 32:8385-8393 (2011).
Bauer et al., "Flocculation and stabilization of colloidal silica by the adsorption of poly-diallyl-dimethyl-ammoniumchloride (PDADMAC) and of copolymers of DADMAC with N-methyl-N-vinylacetamide (NMVA)," Colloid Polym. Sci. 276:698-708 (1998).
Benezra et al., "Multimodal silica nanoparticles are effective cancer-targeted probes in a model of human melanoma," J. Clin. Invest. 121(7):2768-2780 (2011).
Bharali et al., "Organically modified silica nanoparticles: A nonviral vector for in vivo gene delivery and expression in the brain," Proc. Natl. Acad. Sci. USA 102(32):11539-11544 (2005).
Brown et al., "Influence of shape, adhesion and simulated lung mechanics on amorphous silica nanoparticle toxicity," Advanced Powder Technol. 18(1):69-79 (2007).
Burton et al., "Protection from Cancer by 'Silica' in the Water-Supply of U.S. Cities," Journal of Environmental Pathology and Toxicology 4:31-40 (1980).
Carlisle, E.M. "Silicon" in a Handbook of Nutritionally Essential Minerals, edited by B.L. O'Dell & R.A. Sunde; Marcel Dekker: New York, 1997, pp. 603-618, 18 pages.
Chang et al., "In Vitro Cytotoxicitiy of Silica Nanoparticles at High Concentrations Strongly Depends on the Metabolic Activity Type of the Cell Line," Environ. Sci. Technol. 41:2064-2068 (2007).
Cho et al., "The impact of size on tissue distribution and elimination by single intravenous injection of silica nanoparticles," Toxicol. Lett. 189:177-183 (2009).
Choi et al., "Comparison of cytotoxic and inflammatory responses of photoluminescent silicon nanoparticles with silicon micron-sized particles in RAW 264.7 macrophages," J. Appl. Toxicol. 29:52-60 (2009).
Choi et al., "Silica-Based Nanoparticle Uptake and Cellular Response by Primary Microglia," Environ. Health Perspectives 118(5):589-595 (2010).
Christen and Fent, "Silica nanoparticles and silver-doped silica nanoparticles induce endoplasmatic reticulum stress response and alter cytochrome P4501A activity," Chemosphere 87:423-434 (2012).
Chu et al., "Cellular uptake, evolution, and excretion of silica nanoparticles in human cells," Nanoscale 3:3291-3299 (2011).
Chu et al., "Physiological pathway of human cell damage induced by genotoxic crystalline silica nanoparticles," Biomaterials 33:7540-7546 (2012).
Chung et al., "The effect of surface charge on the uptake and biological function of mesoporous silica nanoparticles in 3T3-L1 cells and human mesenchymal stem cells," Biomaterials 28:2959-2966 (2007).
Collins English Dictionary—Complete & Unabridged, 10th ed. (2015). Retrieved Jun. 24, 2015 from Dictionary.com website: http://dictionary.reference.com/browse/silicic acid, 2 pages.
Corbalan et al., "Amorphous silica nanoparticles trigger nitric oxide/peroxynitrite imbalance in human endothelial cells: inflammatory and cytotoxic effects," Int. J. Nanomed. 6:2821-2835 (2011).
Dalwadi et al., "Comparison of Diafiltration and Tangential Flow Filtration for Purification of Nanoparticle Suspensions," Pharm. Res. 22(12):2152-2162 (2005).
de Mesquita and Kerr, "Local effects of silica on tumor growth inhibition. A histological study," Arch. Geschwulstforsch. 45/7:637-647 (1975).
de Sousa Cavalcante and Monteiro, G., Gemcitabine: Metabolism and molecular mechanisms of action, sensitivity and chemoresistance in pancreatic cancer. Eur J Pharmacol 2014; 741C:8-16.
Deng et al., "Differential plasma protein binding to metal oxide nanoparticles," Nanotechnology 20:455101, 9 pages (2009).
Deng et al., "Nanoparticle-induced unfolding of fibrinogen promotes Mac-1 receptor activation and inflammation," Nat. Nanotechnol. 6:39-44 (2011).
Denies S, Cicchelero L, Van Audenhove I & Sanders NN. Combination of interleukin-12 gene therapy, metronomic cyclophosphamide and DNA cancer vaccination directs all arms of the immune system towards tumor eradication. J Control Release 2014; 187:175-82.
Diaz et al., "Assessing Methods for Blood Cell Cytotoxic Responses to Inorganic Nanoparticles and Nanoparticle Aggregates," Small 4(11):2025-2034 (2008).
Downs et al., "Silica nanoparticles administered at the maximum tolerated dose induce genotoxic effects through an inflammatory reaction while gold nanoparticles do not," Mutat. Res. 745:38-50 (2012).
Drescher et al., "Toxicity of amorphous silica nanoparticles on eukaryotic cell model is determined by particle agglomeration and serum protein adsorption effects," Anal. Bioanal. Chem. 400:1367-1373 (2011).
Effati and Pourabbas, "One-pot synthesis of sub-50 nm vinyl- and acrylate-modified silica nanoparticles," Powder Technology 219:276-283 (2012).
Erdogdu and Hasirci, "An Overview of the Role of Mineral Solubility in Silicosis and Asbestosis," Environ. Res. Sect. A 78:38-42 (1998).
Ernst et al., "Pulmonary inflammation in rats after intratracheal instillation of quartz, amorphous SiO2, carbon black, and coal dust and the influence of poly-2-vinylpyridine-N-oxide (PVNO)," Exp. Toxic Pathol. 54:109-126 (2002).
Exley, C. "Reflections upon and recent insight into the mechanism of formation of hydroxyaluminosilicates and the therapeutic potential of silicic acid." Coordination Chemistry Reviews 256: 82-88 (2012).
Fede et al., "The toxicity outcome of silica nanoparticles (Ludox®) is influenced by testing techniques and treatment modalities," Anal. Bioanal. Chem. 404:1789-1802 (2012).

(56) References Cited

OTHER PUBLICATIONS

Flaten and Bolviken, "Geographical Associations Between Drinking Water Chemistry and the Mortality and Morbidity of Cancer and Some Other Diseases in Norway," The Science of the Total Environment 102:75-100 (1991).
Follows, D., et al. "Beta-casein adsorption at the silicon oxide-aqueous solution interface: calcium ion effects." Biomacromolecules (2004); 5: 319-325.
Fruijtier-Pölloth, "The toxicological mode of action and the safety of synthetic amorphous silica—A nanostructured material," Toxicology 294:61-79 (2012).
Gautam et al., "Inhibition of Experimental Lung Metastasis by Aerosol Delivery of PEI-p53 Complexes," Mol. Ther. 2(4):318-323 (2000).
Gao et al., "Influence of surfactant surface coverage and aging time on physical properties of silica nanoparticles." Colloids and Surfaces A: Physicochem. Eng. Aspects (2009); 350: 33-37.
Ghio et al. "Hypothesis: is lung disease after silicate inhalation caused by oxidant generation?" Lancet (1990); 336: 967-969.
Gibson et al., "Enhanced In Vivo Response to Silicate-Substituted Hydroxyapatite," Key Engineering Materials, vols. 218-220, pp. 203-206, 2002.
Gonzalez-Munoz et al., "Beer consumption reduces cerebral oxidation caused by aluminum toxicity by normalizing gene expression of tumor necrotic factor alpha and several antioxidant enzymes," Food Chem. Toxicol. 46:1111-1118 (2008).
Gualtieri et al. "Thermal decomposition of asbestos and recycling in traditional ceramics." Journal of the European Ceramic Society (2000); 20: 1409-1418.
Gulley and Martin, "Stabilization of Colloidal Silica Using Polyols," J. Colloid Interface Sci. 241:340-345 (2001).
He et al., "In Vivo Study of Biodistribution and Urinary Excretion of Surface-Modified Silica Nanoparticles," Anal. Chem. 80:9597-9603 (2008).
Health Canada, Health Products and Food Brach Inspectorate. Good Manufacturing Practices (GMP) Guidelines—2009 Edition, Version 2, 100 pages (2009).
Henrotte et al., "The regulatory role of silicon on the cell cycle," C.R. Acad. Sci. Paris 306:525-528 (1988) (with English Abstract).
Hirai et al., "Amorphous silica nanoparticles size-dependently aggravate atopic dermatitis-like skin lesions following an intradermal injection," Particle Fibre Technol. 9:3, 11 pages (2012).
Huang et al., "The effect of the shape of mesoporous silica nanoparticles on cellular uptake and cell function," Biomaterials 31:438-448 (2010).
Huang et al., "The promotion of human malignant melanoma growth by mesoporous silica nanoparticles through decreased reactive oxygen species," Biomater. 31:6142-6153 (2010).
Hwang et al., "A Physically Transient Form of Silicon Electronics," Science 337:1640-1644 (2012).
Hwang et al., "Anti-Cancer Activity of a Novel Small Molecule Compound That Simultaneously Activates p53 and Inhibits NF-kB Signaling," PLOS One 7(9):e44259, 11 pages (2012).
Iler, "Colloidal Components in Solutions of Sodium Silicate," ACS Symposium Series, vol. 194, Chapter 7, pp. 95-114 (1982).
Iler, R. K., The chemistry of silica: Solubility, polymerisation, colloid and surface properties, and biochemistry. John Wiley & Sons: New York, 1979, p. 11.
International Preliminary Report on Patentability, 8 pages, PCT appl. No. PCT/EP2009/005717 (dated Feb. 1, 2011).
Jacobs and Tomczak, "Evaluation of Bensal HP for the Treatment of Diabetic Foot Ulcers," Adv. Skin Wound Care 21:461-465 (2008).
Jacobson et al., "Short Analytical Review, Epidemiology and Estimated Population Burden of Selected Autoimmune Diseases in the United States" Clinical Immunology and Immunopathology, vol. 84, No. 3, Sept., pp. 223-243, 1997.
Jeong-Hwan et al., "Single and repeated oral dose toxicity studies of titanium dioxide nanoparticles," Toxicol. Lett. 211S:S198, Abs. No. P33-03 (2012).
Jiang L, Yang KH, Guan QL, Mi DH & Wang J. Cisplatin plus etoposide versus other platin-based regimens for patients with extensive small-cell lung cancer: a systematic review and meta-analysis of randomised, controlled trials. Intern Med J 2012; 42:1297-309.
Jugdaohsingh et al., "Oligomeric but not monomeric silica prevents aluminum absorption in humans," Am. J. Clin. Nutr. 71:944-949 (2000).
Jugdaohsingh, R. ("Silicon and bone health," The Journal of Nutrition, Health & Aging 2007, 11, 99-110).
Jugdaosingh, et al., "Is there a Biochemical Role for Silicon?" Metal Ions in Biology and Medicine (2008); 10: 45-55, John Lobbey Eurotext: Montrouge, 13 pages.
Jung et al., "Quantitative Analysis and Efficient Surface Modification of Silica Nanoparticles," J. Nanomater. vol. 2012, Article ID 593471, 8 pages (2012).
Kerek and Voicu, "Sub-Nano Silicic Acid, The Putative Biologically Active Form Of Silica," Basic Clin. Pharmacol. Toxicol. 109(Suppl. 1):26, Abs. No. O10 (2011).
Kim et al., "Comparative study of cytotoxicity, oxidative stress and genotoxicity induced by silica nanomaterials in human neuronal cell line," Mol. Cell Toxicol. 6: 6337-6344 (2010).
Kim et al., "Comparative study on transcriptional responses of human neuronal cells to silica nanoparticles with different stabilizers," BioChip J. 4(4):296-304 (2010).
Kim et al., "Gene expression profiling associated with treatment of positive charged colloidal silica nanoparticle in human neuroblastoma cells," BioChip J. 5(4):317-326 (2011).
Kim, et al., "Polymer Dynamics in PEG-Silica Nanocomposites: Effects of Polymer Molecular Weight, Temperature and Solvent Dilution." Macromolecules (2012); 45: 4225-4237.
Kreuter et al., "Apolipoprotein-mediated Transport of Nanoparticle-bound Drugs Across the Blood-Brain Barrier," J. Drug Target. 10(4):317-325 (2002).
Ku et al., "The blood-brain barrier penetration and distribution of PEGylated fluorescein-doped magnetic silica nanoparticles in rat brain," Biochem. Biophys. Res. Commun. 394:871-876 (2010).
Kumar et al., "In Vivo Biodistribution and Clearance Studies Using Multimodal Organically Modified Silica Nanoparticles," ACS Nano 4(2):699-708 (2010).
Lee et al., "The comparative effects of mesoporous silica nanoparticles and colloidal silica on inflammation and apoptosis," Biomaterials 32:9434-9443 (2011).
Li et al., "Size-dependent cytotoxicity of amorphous silica nanoparticles in human hepatoma HepG2 cells," Toxicology in Vitro 25:1343-1352 (2011).
Lin and Haynes, "Impacts of Mesoporous Silica Nanoparticle Size, Pore Ordering, and Pore Integrity on Hemolytic Activity," J. Am. Chem. Soc. 132:4834-4842 (2010).
Lin et al., "In vitro toxicity of silica nanoparticles in human lung cancer cells," Toxicol. Appl. Pharmacol. 217:252-259 (2006).
Linthicum, "Ultrastructural effects of silicic acid on primary lung fibroblasts in tissue culture," Tissue Cell 33(5):514-523 (2001).
Lison et al., "Nominal and Effective Dosimetry of Silica Nanoparticles in Cytotoxicity Assays," Toxicol. Sci. 104(1):155-162 (2008).
Liu and Sun, "Endothelial cells dysfunction induced by silica nanoparticles through oxidative stress via JNK/P53 and NF-kB pathways," Biomater. 31:8198-8209 (2010).
Liu et al., "Single and repeated dose toxicity of mesoporous hollow silica nanoparticles in intravenously exposed mice," Biomater. 32:1657-1668 (2011).
Lu et al., "Biocompatibility, Biodistribution, and Drug-Delivery Efficiency of Mesoporous Silica Nanoparticles for Cancer Therapy in Animals," Small 6(16):1794-1805 (2010).
Lu et al., "In vitro cytotoxicity and induction of apoptosis by silica nanoparticles in human HepG hepatoma cells," Int. J. Nanomed. 6:1889-1901 (2011).
Lundqvist et al., "Protein Adsorption onto Silica Nanoparticles: Conformational Changes Depend on the Particles' Curvature and the Protein Stability," Langmuir 20:10639-10647 (2004).
Malugin et al., "Differential toxicity of amorphous silica nanoparticles toward phagocytic and epithelial cells," J. Nanopart. Res. 13:5381-5396 (2011).

(56) References Cited

OTHER PUBLICATIONS

Malvindi et al., "SiO2 nanoparticles biocompatibility and their potential for gene delivery and silencing," Nanoscale 4:486-495 (2012).
Mamaeva et al., "Mesoporous silica nanoparticles in medicine—Recent advances," Adv. Drug Deliv. Rev. pii: S0169-409X (2012).
Mansour et al., "Therapy of established B16-F10 melanoma tumors by a single vaccination of CTL/T helper peptides in VacciMax®," J. Translational Med. 5:20, 8 pages (2007).
Martin et al., "Fast aggregation of colloidal silica," Phys. Rev. A. 41(8):4379-4391 (1990).
Martin,"Slow aggregation of colloidal silica," Phys. Rev. A 36(7):3415-3426 (1987).
Martin, K.R., "The chemistry of silica and its potential health benefits." The Journal of Nutrition, Health & Aging (2007); 11 (2): 94-98.
McCarthy et al., "Mechanisms of Toxicity of Amorphous Silica Nanoparticles on Human Lung Submucosal Cells in Vitro: Protective Effects of Fisetin," Chem. Res. Toxicol. 25:2227-2235 (2012).
Millipore, "Protein Concentration and Diafiltration by Tangential Flow Filtration," Technical Brief, 24 pages (2003).
Mitchell et al., "Iron(III)-doped, silica nanoshells: a biodegradable form of silica," J. Am. Chem. Soc. 12 page accepted manuscript (2012).
Mohamed et al., "Activation of stress-related signalling pathway in human cells upon SiO2 nanoparticles exposure as an early indicator of cytotoxicity," J. Nanobiotechnol. 9:29, 14 pages (2011).
Mosby's Medical Dictionary, 8 ed. (2009). Retrieved Jun. 23, 2015 from http://medical-dictionary.thefreedictionary.com/silicic+acid.
Mossman and Glenn (Critical Reviews in Toxicology, 2013, 43 (8), 632-660).
Nabeshi et al., "Amorphous nanosilica induce endocytosisdependent ROS generation and DNA damage in human keratinocytes," Particle Fibre Technol. 8:1, 10 pages (2011).
Nabeshi et al., "Effect of amorphous silica nanoparticles on in vitro RANKL-induced osteoclast differentiation in murine macrophages," Nanoscale Res. Lett 6:464, 5 pages (2011).
Napierska et al., "Oxidative Stress Induced by Pure and Iron-Doped Amorphous Silica Nanoparticles in Subtoxic Conditions," Chem. Res. Toxicol. 25:828-837 (2012).
Napierska et al., "Size-Dependent Cytotoxicity of Monodisperse Silica Nanoparticles in Human Endothelial Cells," Small 5(7):846-853 (2009).
Napierska et al., "The nanosilica hazard: another variable entity," Particle Fibre Technol. 7:39, 32 pages (2010).
National Cancer Institute (definition: solid tumor; accessed 2011), 1 page.
Office Action for EP Application No. 08840441.3, dated Nov. 27, 2013, 5 pages.
Orr et al., "Cellular recognition and trafficking of amorphous silica nanoparticles by macrophage scavenger receptor A," Nanotoxicol. 5(3):296-311 (2011).
Park and Park, "Oxidative stress and pro-inflammatory responses induced by silica nanoparticles in vivo and in vitro," Toxicol. Lett. 184:18-25 (2009).
Park et al., "In vitro developmental toxicity test detects inhibition of stem cell differentiation by silica nanoparticles," Toxicol. Appl. Pharmacol. 240:108-116 (2009).
Park et al., "In vitro evaluation of cytotoxic and inflammatory properties of silica nanoparticles of different sizes in murine RAW 264.7 macrophages," J. Nanopart. Res. 13:6775-6787 (2011).
Passagne et al., "Implication of oxidative stress in size-dependent toxicity of silica nanoparticles in kidney cells," Toxicology 299:112-124 (2012).
Patwardhan et al., "Chemistry of Aqueous Silica Nanoparticle Surfaces and the Mechanism of Selective Peptide Adsorption," J. Am. Chem. Soc. 134:6244-6256 (2012).
Pavelić et al. "Natural zeolite clinoptilolite: new adjuvant in anti-cancer therapy." J. Mol. Med. (2001); 78: 708-720.
Quignard et al., "Long-term fate of silica nanoparticles interacting with human dermal fibroblasts," Biomater. 33:4431-4442 (2012).
Rabolli et al., "The cytotoxic activity of amorphous silica nanoparticles is mainly influenced by surface area and not by aggregation," Toxicol Lett. 206:197-203 (2011).
Rancan et al., "Skin Penetration and Cellular Uptake of Amorphous Silica Nanoparticles with Variable Size, Surface Functionalization, and Colloidal Stability," ACS Nano 6(8):6829-6842 (2012).
Reffitt et al., "Orthosilicic acid stimulates collagen type 1 synthesis and osteoblastic differentiation in human osteoblast-like cells in vitro," Bone 32:127-135 (2003).
Rimstidt et al. "The kinetics of silica-water re3astions." Geochimica et Cosmochimica Acta (1980); 44(11): 1683-1699 (Abstract).
Rochow, E.G. The chemistry of silicon. Pergamon Texts in Inorganic Chemistry vol. 9, Pergamon: Oxford. 1973, p. 1345-1346, 8 pages.
Rose et al., "Dietary glycine inhibits the growth of B16 melanoma tumors in mice," Carcinogenesis 20(5):793-798 (1999).
Rosen et al. "High-dose methotrexate with citrovorum factor rescue and Adriamycin in childhood osteogenic sarcoma." Cancer (1974); 33: 1151-1163.
Sandberg et al., "Comparison of non-crystalline silica nanoparticles in IL-1β release from macrophages," Particle Fibre Toxicol. 9:32, 13 pages (2012).
Schaefer et al., "Fractal Geometry of Colloidal Aggregates," Phys. Rev. Lett. 52(26):2371-2374 (1984).
Schlegel, "Aus der Praxis—Fur die Praxis. Grundlegende Krebsbehandlung," Hippokrates (Helsinki) 24(10):300-304 (1953) (with English translation), 19 pages.
Schubbe et al., "Size-Dependent Localization and Quantitative Evaluation of the Intracellular Migration of Silica Nanoparticles in Caco-2 Cells," Chem. Mater. 24:914-923 (2012).
Seliger et al., "Characterization of the Major Histocompatibility Complex Class I Deficiencies in B16 Melanoma Cells," Cancer Res. 61:1095-1099 (2001).
Shang et al., "Unfolding of Ribonuclease A on Silica Nanoparticle Surfaces," Nano Lett. 7(7):1991-1995 (2007).
Shemetov et al., "Molecular Interaction of Proteins and Peptides with Nanoparticles," ACS Nano 6(6):4585-4602 (2012).
Simpson et al. "Therapy of spontaneous mouse cancer." Annals of Surgery (1931); 93: 169-179.
So et al., "Effect of Micro/Nano Silica Particle Feeding for Mice," J. Nanosci. Nanotechnol. 8:5367-5371 (2008).
Sohaebuddin et al., "Nanomaterial cytotoxicity is composition, size, and cell type dependent," Particle Fibre Toxicol. 7:22, 17 pages (2010).
SS 20 Powder sodium silicate MSDS (National Silicates 2008), 5 pages.
Stober and Fink,"Controlled Growth of Monodisperse Silica Spheres in the Micron Size Range," J. Colloid Interface Sci. 26:62-69 (1968).
Sun et al., "Cytotoxicity and mitochondrial damage caused by silica nanoparticles," Toxicol. In Vitro 25:1619-1629 (2011).
Svensson, O., Kurut, A., and Skepb, M. (2014). Adsorption of β-casein to hydrophilic silica surfaces. Effect of pH and electrolyte. Food Hydrocolloids 36: 332-338.
Tacke, R. (1999). Milestones in the Biochemistry of Silicon: From Basic Research to Biotechnological Applications. Angew. Chem. Int. Ed. 38: 3015-3018.
Tamba et al., "New Experimental Data On The Bioavailability And Blood Brain Barrier Penetration Of A Systemically Administered Silica Nanoparticles," Basic Clin. Pharmacol. Toxicol. 109(Suppl. 1):132, Abs. No. P231 (2011).
Taylor et al., "Soluble Silica with High Affinity for Aluminum under Physiological and Natural Conditions," J. Am. Chem. Soc. 119:8852-8856 (1997).
Thamatrakoln and Hildebrand, "Analysis of Thalassiosira pseudonana Silicon Transporters Indicates Distinct Regulatory Levels and Transport Activity through the Cell Cycle," Eukaryotic Cell 6(2):271-279 (2007).
Thomassen et al., "Letter to the Editor Regarding the Article by Wittmaack," Chem. Res. Toxicol. 25:4-6 (2012).

(56) References Cited

OTHER PUBLICATIONS

Tiberg, F., Nylander, T., Su, T. J., Lu, J. R., and Thomas, R. K. (2001). Beta-casein adsorption at the silicon oxide-aqueous solution interface. Biomacromolecules. 2: 844-50.
Trewyn et al., "Biocompatible mesoporous silica nanoparticles with different morphologies for animal cell membrane penetration," Chem. Eng. J. 137:23-29 (2008).
Uboldi et al., "Amorphous silica nanoparticles do not induce cytotoxicity, cell transformation or genotoxicity in Balb/3T3 mouse fibroblasts," Mutation Res. 745:11-20 (2012).
Uekawa et al., "Synthesis and Characterization of Titania-Sugar Alcohol Complex Nanoparticles." J. Ceramic Soc. Jpn. 114(10):807-813 (2006).
Uppal et al., "Photodynamic Action of Rose Bengal Silica Nanoparticle Complex on Breast and Oral Cancer Cell Lines," Photochem. Photobiol. 87:1146-1151 (2011).
Vail, J. G., Soluble Silicates in Industry. American Chemical Society Monograph Series. The Chemical Catalog Company: New York, 1928, p. 443, 5 pages.
Van Den Boorn et al., "Effective Melanoma Immunotherapy in Mice by the Skin-Depigmenting Agent Monobenzone and the Adjuvants Imiquimod and CpG," PLOS One 5(5):e10626, 12 pages (2010).
Vlasova et al., "The Adsorption of Biogenic Amines on the Surface of Highly Dispersed Silica from Aqueous Solutions," Colloid J. 68(3):384-386 (2006).
Wang et al., "Oxidative mechanisms contribute to nanosize silican dioxide-induced developmental neurotoxicity in PC12 cells," Toxicol in Vitro 25:1548-1556 (2011).
Wang et al., "Oxidative stress contributes to silica nanoparticle-induced cytotoxicity in human embryonic kidney cells," Toxicol. in Vitro 23:808-815 (2009).
Wang et al., "Silica Nanoparticles Suppress Fibronectin-Mediated Adhesion and Migration in Normal Human Keratinocytes," J. Nanosci. Nanotechnol. 12:293-299 (2012).
Waters et al., "Macrophage Responses to Silica Nanoparticles are Highly Conserved Across Particle Sizes," Toxicol. Sci. 107(2):553-569 (2009).
Windholz, M., The Merck Index, 10th ed., Merck & Co: New Jersey, 1983, 8326, pp. 1220 and 1221, 4 pages.
Windholz, M., The Merck Index. Merck & Co.: New Jersey, 1983, pp. 1220 and 1241, 3 pages.
Winslow, "New Cancer Drugs Use Body's Own Defenses," Wall Street Journal, 2 pages (2012).
Wittmaack, "Excessive Delivery of Nanostructured Matter to Submersed Cells Caused by Rapid Gravitational Settling," ACS Nano 5(5):3766-3778 (2011).
Wittmaack, "Novel Dose Metric for Apparent Cytotoxicity Effects Generated by in Vitro Cell Exposure to Silica Nanoparticles," Chem. Res. Toxicol. 24:150-158 (2011).
Wittmaack, "Reply to the Letter to the Editor Regarding My Article on Dose Metrics in Nanotoxicity Studies (Wittmaack, 2011)," Chem. Res. Toxicol. 25:7-10 (2012).
Wottrich et al., "Biological effects of ultrafine model particles in human macrophages and epithelial cells in mono- and co-culture," Int. J. Hyg. Environ. Health 207:353-361 (2004).
Wu et al., "Neurotoxicity of Silica Nanoparticles: Brain Localization and Dopaminergic Neurons Damage Pathways," ACS Nano 5(6):4476-4489 (2011).
Xiao et al., "Dodecagonal tiling in mesoporous silica," Nature 487:349-353 (2012).
Xie et al., "Biodistribution and toxicity of intravenously administered silica nanoparticles in mice," Arch. Toxicol. 84:183-190 (2010).
Xu et al., "Effects of nano-sized silicon dioxide on the structures and activities of three functional proteins," J. Hazard. Mater. 180:375-383 (2010).
Xu et al., "Effects of $SiO_2$ nanoparticles on HFL-I activating ROS-mediated apoptosis via p53 pathway," J. Appl. Toxicol. 32:358-364 (2012).
Yang et al., "Comparative study of cytotoxicity, oxidative stress and genotoxicity induced by four typical nanomaterials: the role of particle size, shape and composition," J. Appl. Toxicol. 29:69-78 (2009).
Ye et al., "In vitro toxicity of silica nanoparticles in myocardial cells," Environ. Toxicol. Pharmacol. 29:131-137 (2010).
Ye et al., "Nano-$SiO_2$ induces apoptosis via activation of p53 and Bax mediated by oxidative stress in human hepatic cell line," Toxicol. in Vitro 24:751-758 (2010).
Yu et al., "Impact of Silica Nanoparticle Design on Cellular Toxicity and Hemolytic Activity," ACS Nano 5(7):5717-5728 (2011).
Yu et al., "Influence of Geometry, Porosity, and Surface Characteristics of Silica Nanoparticles on Acute Toxicity: Their Vasculature Effect and Tolerance Threshold," ACS Nano 6(3):2289-2301 (2012).
Yu et al., "Toxicity of amorphous silica nanoparticles in mouse keratinocytes," J. Nanopart. Res. 11:15-24 (2009).
Zangi and Filella, "Transport routes of metalloids into and out of the cell: A review of the current knowledge," Chemico-Biol. Interact. 197:47-57 (2012).
Zhang et al., "Processing pathway dependence of amorphous silica nanoparticle toxicity—colloidal versus pyrolytic," J. Am. Chem. Soc. Accepted manuscript, 48 pages (2012).
Zhang et al., "ZnO, $TiO_2$, $SiO_2$, and $Al_2O_3$ Nanoparticles-induced Toxic Effects on Human Fetal Lung Fibroblasts," Biomed. Environ. Sci. 24(6):661-669 (2011).
Partial European Search Report for European Application No. 17184331.1 dated Feb. 26, 2018.
Extended European Search Report for European Application No. 17184331.1 dated May 29, 2018.
PCT/US2008/079802, International Search Report dated Nov. 25, 2009, 7 pages.
PCT/US2008/079802, Written Opinion dated Nov. 25, 2009, 9 pages.
PCT/US2008/079802, International Preliminary Report on Patentability dated Apr. 20, 2010, 10 pages.

\* cited by examiner

Subcutaneous Melanoma

Treated Horse Before Treatment

A-Inside of Right Hind
B-Outside of Left Hind
C-Outside of Right Hind & Inside of Left Hind
D-Inside of Right Hind Treated Horse Two Weeks After Treatment Treatment Protocol:

Application of a light spray of a solution of 0.5 mg/ml of Sodium Silicate, pH 7.6, to the lower portion of each hind leg once a day for two days.

Right and left hind leg denoted by RH and LH respectively

CONTROL HORSE

A- BEFORE  B&C- AFTER TWO WEEKS WITHOUT TREATMENT

FIGURE 8
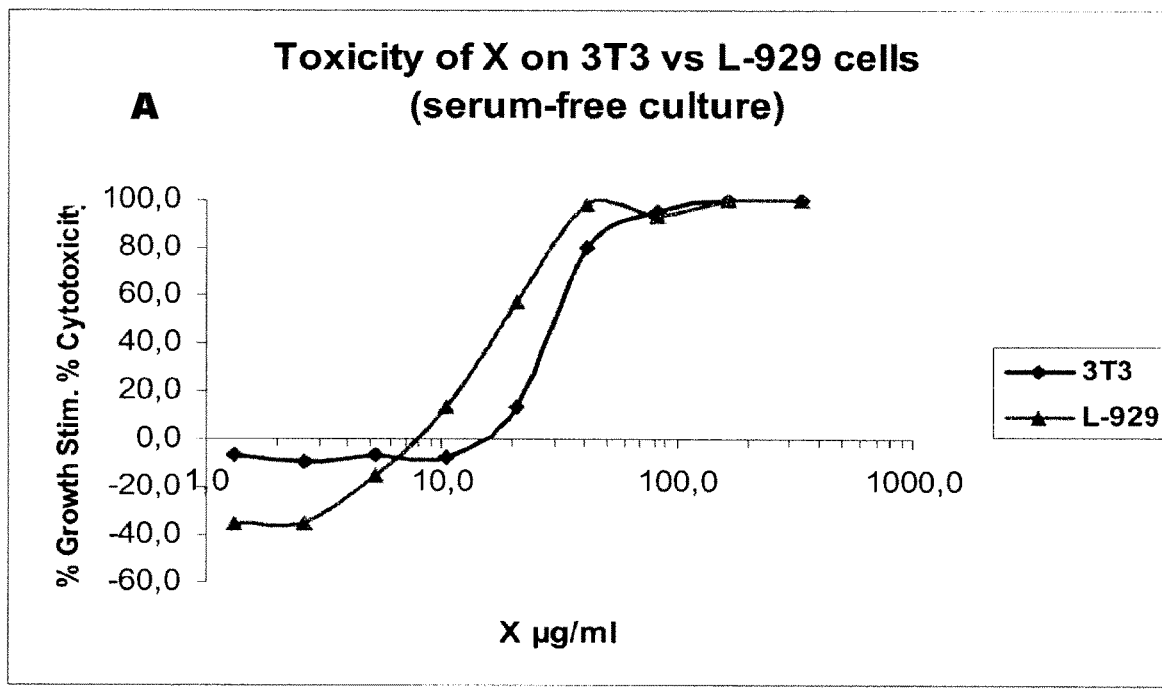
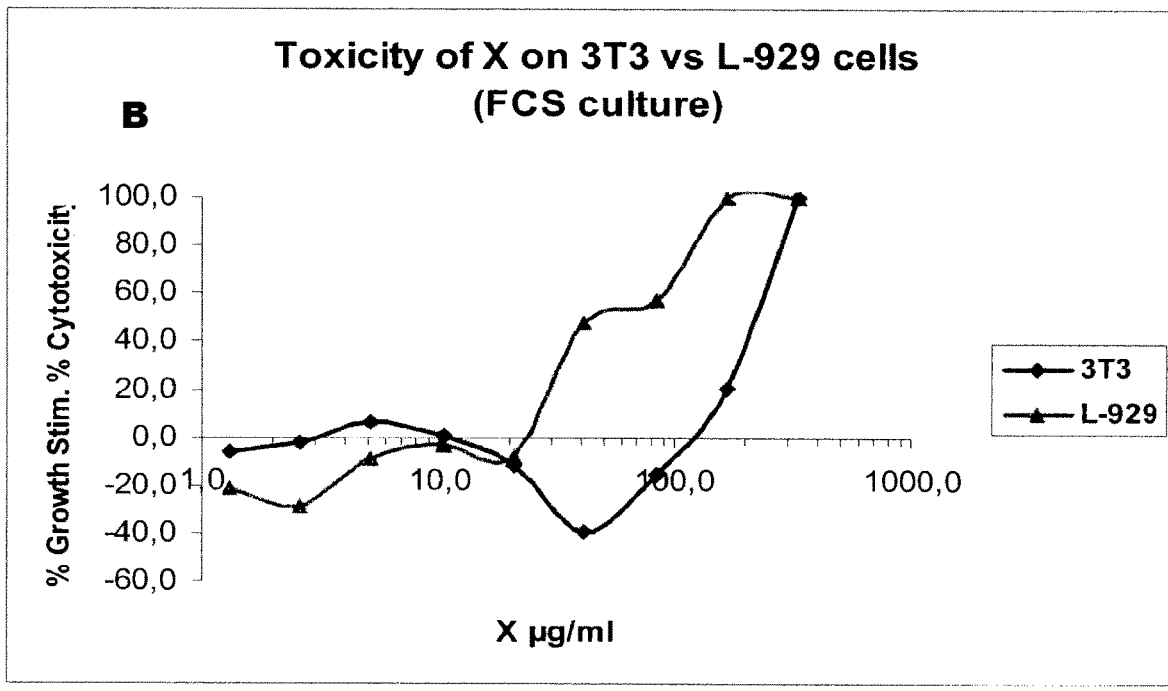

SILICATE CONTAINING COMPOSITIONS AND METHODS OF TREATMENT

CROSS-REFERENCE TO RELATED PATENT APPLICATIONS

This application is a continuation of U.S. application Ser. No. 15/856,598, filed Dec. 28, 2017, which is a continuation of U.S. application Ser. No. 12/250,624, filed Oct. 14, 2008, now U.S. Pat. No. 9,889,151, which claims priority from U.S. Provisional Patent Application Nos. 60/960,794, filed Oct. 15, 2007, 61/071,754, filed May 15, 2008, 61/090,833, filed Aug. 21, 2008. These applications are incorporated herein by reference in their entirety.

FIELD OF THE INVENTION

The present invention relates compositions comprising a silicate and methods of use thereof. In particular, the compositions of the present invention are suitable for treating inflammatory conditions, cancer, bacterial and viral infections, and infected and uninfected wounds. The compositions of the present invention are also useful in treating spinal cord injury, tissue remodeling, and promoting bone growth and repair.

BACKGROUND OF THE INVENTION

Antibiotic resistant infections are a global clinical and public health problem that has emerged with alarming rapidity in recent years and undoubtedly will increase in the near future. For example, bacterial infections caused by methicillin-resistant Staphylococci, such as methicillin-resistant *Staphylococcus aureus* (MRSA), are increasing in prevalence in both the hospital and community settings. Staphylococci are found on the skin and within the digestive and respiratory tracts but can infect open wounds and burns and can progress to serious systemic infection. The emergence of multi-drug resistant Staphylococci, especially, in the hospital where antibiotic use is frequent and this selective pressure for drug-resistant organism is high, has proven a challenge for treating these patients. The presence of MRSA on the skin of patients and health care workers has promoted transmission of multi-drug resistant organisms in health care settings.

Likewise, other antibiotic resistant bacteria, such as ciprofloxacin-resistant, and/or vancomycin-resistant strains are making current treatments less effective in combating infections arising from these microorganisms. And because drug resistant micro-organisms is a growing problem, the morbidity, mortality, and financial costs of such infections pose an increasing burden for health care systems worldwide. Strategies to address these issues emphasize enhanced surveillance of resistance, increased monitoring and improved usage of antimicrobial drugs, professional and public education, development of new drugs, and assessment of alternative therapeutic modalities. Accordingly, there is a need in the art for additional therapies for treating and preventing a bacterial infection.

Additionally, there is a need in the art for cancer therapeutic agents. Cancer is characterized by unrestricted cell growth and many cancer therapies work by inhibiting cell division. Although new therapeutics focus on inhibiting cell division because normal cells do not divide after maturation, normal cells are nevertheless affected by antitumor agents. And there is tremendous variability in the efficacy of certain chemotherapeutic agents; some drugs are more effective than others for certain patients, for certain cancers, or at certain stages of treatment.

Continuing, inflammation comes as the immune system's first response to infection or irritation. Inflammatory diseases are typically characterized by one or more of the following symptoms: redness, swollen joints warm to the touch, joint pain, joint stiffness, and loss of joint function. While several treatments are currently available to decrease joint pain, swelling and inflammation, such as non-steroidal anti-inflammatory drugs (NSAIDs), corticosteroids (e.g., prednisone), anti-malarial agents (e.g., hydroxychloroquine), and acetaminophen, their strong side effects often limit their use.

In fact, autoimmune diseases (e.g. rheumatoid arthritis, systemic lupus erythematosus, multiple sclerosis, glomerulonephritis, inflammatory bowel diseases (Morbus Cohn, colitis ulcerosa), psoriasis) are among the major health problems worldwide. Autoimmune diseases are among the ten leading causes of death. Most of autoimmune diseases require lifelong treatment (Jacobson D L, Gange S J, Rose N R, Graham N M. Clin Immunol Immunopathol 1997; 84:223-43). The standard of care for treating many autoimmune diseases includes a regimen containing anti-inflammatory agents.

Accordingly, because the effective treatment of many diseases and disorders remains a challenge in modern medicine, there is also a need in the art for additional agents for treating cancer and autoimmune and inflammatory conditions. The present invention satisfies that need.

The inventors of the present invention surprisingly found that silicate itself is useful in treating a number of conditions. While Gibson et al. previously reported that the bioactivity of hydroxyapatite is enhanced by the incorporation of silicate ions into a hydroxyapatite lattice, Gibson did not recognize the therapeutic value of silicate alone, or the use of silicate in treating a number of other conditions, including bacterial infections and cancer. See, for example, Gibson et al., *Key Eng. Mater.* 218-220 (2002) 203-206.

Furthermore, Bensal HP (containing salicylic acid, benzoic acid, PEG and QRB-7 (red oak bark extract)) is being sold for use in complications associated with pyodermas, and Lexaderm (containing salicylic acid, benzoic acid, and QRB-7) is being sold as an anti-bacterial, anti-fungal, anti-inflammatory ointment for veterinary use. These compositions, however, do not contain silicate alone and it would not have been possible to identify silicate as an active ingredient in these compositions based on reverse engineering Bensal HP, Lexaderm, or QRB-7, or any of the individual elements in these compositions.

U.S. Pat. Nos. 5,658,896 and 5,534,509 disclose the use of silicate polymers that may be used to treat certain diseases but do not disclose silicate containing compositions that are not polymerized or their use in treating cancer.

SUMMARY OF THE INVENTION

The present invention describes in one embodiment a pharmaceutical composition consisting essentially of

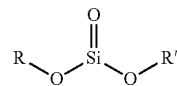

and a pharmaceutically acceptable excipient, wherein R and R' are independently selected from the group consisting of H, a monovalent cation such as a sodium or potassium ion, a divalent cation, a quaternary ammonium group, or an organic fragment. Exemplary cations include, but are not limited to aluminum, calcium, lithium, magnesium, potassium, sodium, zinc and tetraalkyl ammonium salts such as the tetramethyl ammonium group or tetrabutyl ammonium group.

The compositions of the present invention are not an extract of oak bark, such as a red or white oak bark extract, or the oak bark extracts disclosed in U.S. Pat. Nos. 7,014,870, 6,149,947, or U.S. Pat. No. 5,080,900.

Also described herein is a method of treating a sunburn, an inflammatory condition, autoimmune disease, a bacterial or viral infection, or cancer (including a solid tumor such as a melanoma and carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, neuroblastomas, and the like) comprising administering a composition that liberates a silicate anion ($SiO_3^{2-}$) in vivo, wherein the silicate anion is the active ingredient. In one embodiment, the composition comprises a silicate salt, such as sodium, potassium, or lithium silicate salt. In another embodiment, the composition consists essentially of a silicate salt.

The composition according to the present invention can be administered parenterally, such as topically, intravenously or subcutaneously.

Also contemplated in the present invention is a method for healing an infected or uninfected wound, or reducing scar tissue formation, that comprises administering a composition that liberates a silicate anion ($SiO_3^{2-}$) in vivo, wherein the silicate anion is the active ingredient. The wound can be a skin ulcer, such as a decubitus ulcer, diabetic skin ulcer, burn ulcer, traumatic ulcer, crural ulcer, diabetic gangrene, or a surgical site wound.

In another embodiment, the present invention describes a method for inducing an anti-inflammatory response or a method for causing activation of a macrophage, comprising administering a composition that liberates a silicate anion ($SiO_3^{2-}$) in vivo, wherein the silicate anion is the active ingredient.

BRIEF DESCRIPTION OF THE DRAWINGS

FIG. 8. Graph depicting toxicity of sodium silicate on 373 and L-929 cells in (A) serum-free culture and (B) fetal calf serum culture.

DETAILED DESCRIPTION OF THE INVENTION

Introduction

Figure 1:
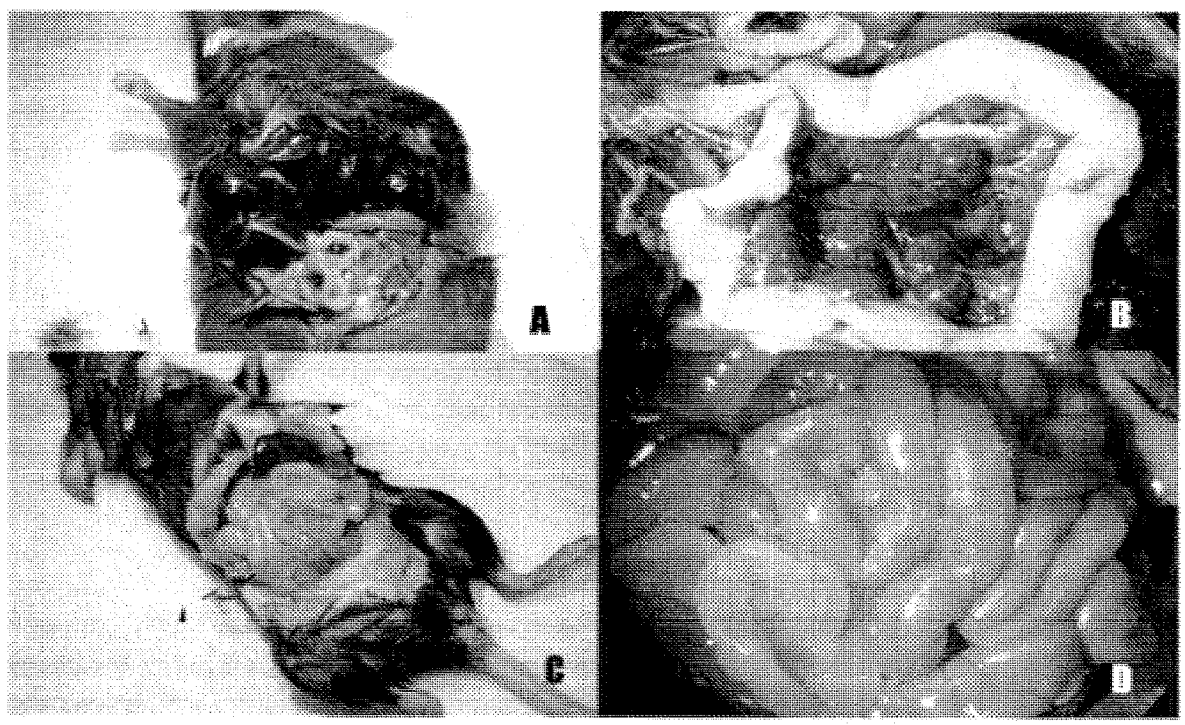
FIG. 1. Close up of intestinal region of untreated (A and B) and treated (C and D) mice containing B16 melanoma cells. Treated mice were administered 100 μg, 135 μg and 135 μg sodium silicate for three consecutive days, respectively, following injection of B16 cells.

The present inventors have surprisingly discovered that a silicate is suitable for treating various diseases or disorders, including an inflammatory condition, autoimmune disease, a bacterial or viral infection, cancer, and infected and uninfected wounds. The compositions of the present invention are also suitable for recruiting macrophages and promoting functional recovery and/or minimizing neurological damage from a spinal cord injury, for tissue remodeling, and for aiding in bone formation and calcification.

Without wishing to be bound by any theory, the inventors hypothesize that compositions of the present invention stimulate the innate immune system. The innate immune system is a "primitive" immune system in that it evolved first and contains cells that react against foreign antigens in a non-specific way. Cells of the innate immune system are present prior to exposure to the antigen, and include phagocytic cells such as macrophages, neutrophils, and natural killer cells. The innate immune system defends host from infection by other organisms, as well as "fight" a number of conditions such as cancer and inflammatory conditions; this natural immunity defends individuals from hostile environment.

Thus, the compositions of the present invention ultimately result in macrophage activation, and are therefore suitable for treating a variety of conditions that would be prevented, treated, or at least alleviated by prophylaxis or treatment with another agent that activates the innate immune system.

For example, as tumors grow, they produce macrophage attracting factor (MAF) as part of the angiogenic process in turn, draw monocytic cells such as macrophages to the tumor in the body's attempt to fight the condition. Because it is hypothesized that the compositions described herein activate macrophages, the present invention is broadly applicable for use in preventing or treating a variety of cancers, including alleviating the severity of the disease.

Similarly, macrophages normally patrol the body in search of foreign, non-self antigens, typically bacteria. The macrophages phagocytize the bacteria, which are then digested to smaller antigenic portions in the lysosome and cycled back to the surface for presentation to the humoral and cellular arms of the immune system. Accordingly, the compositions of the present invention are suitable for treating a large number of bacterial and viral conditions as well.

Compositions

Silicate

A silicate is a compound in which the anionic portion contains one or more central silicon atoms surrounded by electronegative ligands. In one embodiment, accordingly, the anionic portion of the silicate of the present invention contains one central silicon atom surrounded by 3 oxygen atoms.

The silicate of the present invention contains an anionic portion associated with other ions or compounds, such as organic fragments, peptides, proteins (including antibodies), and the like, that satisfy silicate anion valency. For example, exemplary ions that can charge balance a silicate anion include, but are not limited to any monovalent cation such as lithium, sodium and potassium, any divalent cation such as calcium or magnesium, and quaternary ammonium groups, such as tetralkylammonium, $N(CH_3)_4$, $N(butyl)_4$, etc. In other words, the ion or compound associated with the silicate anion can be any cation or organic group that satisfies silicate anion valency.

The compositions for use in the therapeutic methods of the present invention liberate a silicate anion in vivo, wherein the silicate from which the anion was derived is the active ingredient; the silicates of the present invention have the therapeutic effect. The silicate anion can be $(SiO_3)^{-2}$ and/or $(ROSiO_2)^-$, wherein the R group can be any cation or organic group that satisfies silicate anion valency. The silicate anion may or may not re-associate with other components in the body following administration.

In other embodiments, the invention contemplates a pharmaceutical composition comprising a pharmaceutically acceptable excipient and a compound according to Formula I:

$$SiO_x(OR'')_{4-2x} \quad (I)$$

wherein x is 0 or 1. Each occurrence of R" independently is selected from the group consisting of H, a monovalent cation, a quaternary ammonium group, and an organic fragment. Alternatively, two R", taken together, represent a divalent ion.

Examples of monovalent cations include but are not limited to metal ions such as lithium, sodium and potassium ions. Exemplary divalent cations include but are not limited to calcium, magnesium, and zinc ions.

Tetraalkyl ammonium ions are well known in the art. Exemplary ions in this regard feature straight or branched $C_{1-8}$-alkyl substituents, such as methyl, ethyl, propyl, butyl, and octyl. For instance, the ion can be tetramethyl ammonium or tetrabutyl ammonium.

"Organic fragments" as defined herein encompasses typical chemical moieties that are amenable to use in silicon oxides such as formula I above. Accordingly, in some embodiments, an organic fragment is one selected from the group consisting of —$C(O)R^1$, —$C(O)OR^1$, —$C(O)N(R^1)_2$, $C_{1-16}$-alkyl, and phenyl. Substituent $R^1$ in each instance as used herein is H or a straight or branched $C_{1-8}$-alkyl. In one embodiment, the organic fragment is $C_{1-16}$-alkyl, such as $C_{1-8}$-alkyl. Exemplary alkyl groups include methyl, ethyl, butyl, and octyl.

In one embodiment, "x" in Formula I is 0. Accordingly, the compound of Formula I is $Si(O)(OR'')_2$. When R" in each instance is H, the compound is commonly known as silicic acid. Thus, compounds in which R" is an organic fragment or ion are often referred to as silicates.

In another embodiment, "x" in Formula I is 1. Accordingly, the compound of Formula I is $Si(OR'')_2$. When R" in each instance is H in this embodiment, the compound is commonly known as orthosilicic acid, and so compounds in which one or more R" is other than H are often referred to as orthosilicates.

The compositions of the present invention can also be formulated as a prodrug. As used herein, the term "prodrug" means a derivative of a compound that can hydrolyze, oxidize, or otherwise react under biological conditions (in vitro or in vivo) to provide an active compound, particularly a silicate anion. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmbh), which are incorporated by reference herein in their entirety.

As used herein, "w/v" means weight/volume, such that "1% w/v" means 1 gram of the specified ingredient in 100 ml of the volume of liquid. Similarly, "w/w" means weight/weight, such that "1% w/w" means 1 gram of the specified ingredient in 100 g of total weight of the formulation.

The pharmaceutical compositions of the present invention consist essentially of silicate or a compound of Formula I as the active ingredient. In another embodiment, the pharmaceutical compositions of the present invention comprise a silicate or a compound of Formula I, wherein the composition comprises 0.003% w/v to about 50% w/v, about 0.01% w/v to about 50% w/v, about 0.02% w/v to about 50% w/v, 0.05% w/v to about 50% w/v, 0.1% w/v to about 50% w/v silicate or a compound of Formula I, 0.5% w/v to about 45% w/v silicate or a compound of Formula I, about 1.5% to about 45%, about 2% w/v to about 50% w/v silicate or a compound of Formula I, about 3% w/v to about 50% w/v silicate or a compound of Formula I, about 5% w/v to about 50% w/v silicate or a compound of Formula I; about 4% w/v to about 50% w/v silicate or a compound of Formula I, about 5% w/v to about 50% w/v silicate or a compound of Formula I, about 6% w/v to about 50% w/v silicate or a compound of Formula I, about 7% w/v to about 50% w/v silicate or a compound of Formula I, about 8% w/v to about 50% w/v silicate or a compound of Formula I, about 10% w/v to about 50% w/v silicate or a compound of Formula I, about 15% w/v to about 50% w/v silicate or a compound of Formula I, about 20% w/v to about 50% w/v silicate or a compound of Formula I, 0.005% w/v to about 0.025% w/v, about 0.01% w/v to about 0.02% w/v, or about 0.0125% w/v to about 0.0175% w/v. In this context, the term "about" connotes +/−0.005%.

In another embodiment, the pharmaceutical composition comprises at least 0.003% w/v silicate or a compound of Formula I, at least 0.005% w/v silicate or a compound of Formula I, at least about 0.01% w/v silicate or a compound of Formula I, at least about 0.02% w/v silicate or a compound of Formula I, at least about 0.05% w/v silicate or a compound of Formula I, at least about 0.1% w/v silicate or a compound of Formula I, at least about 0.5% w/v silicate or a compound of Formula I, at least about 1.0% silicate or a compound of Formula I, at least about 2.0% w/v silicate or a compound of Formula I, at least about 3.0% w/v silicate or a compound of Formula I, at least about 4.0% w/v silicate or a compound of Formula I, at least about 5.0% w/v silicate or a compound of Formula I, at least about 6.0% w/v silicate or a compound of Formula I, at least about 7.0% w/v silicate or a compound of Formula I, at least about 8.0% w/v silicate or a compound of Formula I, at least about 9.0% w/v silicate or a compound of Formula I, at least about 10.0% w/v silicate or a compound of Formula I, at least about 12.0% w/v silicate or a compound of Formula I, at least about 13.0% w/v silicate or a compound of Formula I, at least about 15.0% w/v silicate or a compound of Formula I, at least about 20% w/v silicate or a compound of Formula I, at least about 25% w/v silicate or a compound of Formula I, at least about 30% w/v silicate or a compound of Formula I, at least about 35% w/v silicate or a compound of Formula I, at least about 40% w/v silicate or a compound of Formula I, or at least about 45% w/v silicate or a compound of Formula I. In this context, the term "about" connotes +/−0.005%.

Method of Making
Dosage and Formulations

An appropriate dosage level will generally be from about 0.001 to about 100 mg per kg patient body weight per day which can be administered in single or multiple doses. Preferably, the dosage level will be from about 0.01 to about 25 mg/kg per day; more preferably from about 0.05 to about 10 mg/kg per day. A suitable dosage level may be from about 0.01 to about 25 mg/kg per day, about 0.05 to about 10 mg/kg per day, or about 0.1 to about 5 mg/kg per day. Within this range the dosage may be from about 0.005 to about 0.05, about 0.05 to about 0.5 or about 0.5 to about 5.0 mg/kg per day. In this context, the term "about" connotes +/−1% mg/kg.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The pH of the compositions of the present invention are preferably at physiological pH, or in the range of about 4.0-10.0, 6.0-8.0, more preferably 6.5-7.8, and most preferably, 6.8-7.4. Additionally, all silicate or Formula I containing solutions when prepared are ultrafiltered to remove polymeric or aggregated material. The silicate or Formula I containing solutions are in the range of about 1-5 mg/ml, preferably 1-3 mg/ml, more preferably 1-2 mg/ml and most preferably 1 mg/ml. In some embodiments, the silicate and Formula I containing solutions are less than 1 mg/ml, such as about 0.05 mg/ml to about 1 mg/ml.

Pharmaceutical compositions and single unit dosage forms comprising silicate or a compound of Formula I as the active ingredient are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or local application (direct injection, microsurgery techniques, or topical application, including topical application to the surface of a skin as well as topical application to an exposed organ or wound). The present invention also contemplates a method for targeted delivery of a silicate or a compound of Formula I, such as a local drug delivery system that directs delivery of the silicate or a compound of Formula I to a particular target. An example of such a mechanism includes a catheter based drug delivery system, a silicate or a compound of Formula I coated implant, and silicate or a compound of Formula I coated suture material.

Other examples include the addition of a silicate or a compound of Formula I containing composition of the present invention for use in biomaterials that are utilized for tissue repair following severe bone fractures, cartilage loss, and for porous matrices as a scaffolding material. Applicants believe that any biomaterial comprising a porous biocompatible composite material which is designed for use as a matrix for tissue regeneration can achieve a more rapid and higher quality desired tissue growth by treating the biomaterial with an effective amount of a silicate or a compound of Formula I.

Exemplary biocompatible composite materials are from carbon microfibers, ceramics, calcium phosphates, metal oxides, and collagen polymers. Preferably, the porosity of the biomaterial such as a ceramic has openings or pores of about 100 to about 2,000 microns in diameter. Included within the concept of "biomaterial" is the use of bone grafts taken from cadaver donors or other sources.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Other vehicles include acetone, ethanol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to topical pharmaceutical compositions and dosage forms if desired. Examples of such additional ingredients are well known in the art. See, e.g., Remington's Pharmaceutical Sciences, 18th eds., Mack Publishing, Easton Pa. (1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Preferred pH ranges are described above. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Formulations for injection may be presented in unit dosage form, e.g., in ampules or in multi-dose containers, optionally with an added preservative. The composition of this invention may take such forms as suspensions, solutions or emulsions in oily or aqueous vehicles, as described above, and may contain formulatory agents such as suspending, stabilizing and/or dispersing agents. The composition may also be formulated using a pharmaceutically acceptable excipient. Such excipients are well known in the art, but typically will be a physiologically tolerable aqueous solution. Physiologically tolerable solutions are those which are essentially non-toxic. Preferred excipients can be either be inert or enhancing.

Pharmaceutical compositions of the invention that are suitable for oral administration can be presented as discrete dosage forms, including, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Controlled release formulations are also contemplated in the present invention. Controlled-release pharmaceutical products can improve drug therapy over that achieved by their non-controlled counterparts. Ideally, the use of an optimally designed controlled-release preparation in medical treatment is characterized by a minimum of drug (compound containing the active ingredient or the active ingredient alone) being employed to cure or control the condition in a minimum amount of time. Advantages of controlled-release formulations include extended activity of the active ingredient, reduced dosage frequency, and increased patient compliance. In addition, controlled-release formulations can be used to affect the time of onset of action or other characteristics, such as blood levels of the active ingredient, and can thus affect the occurrence of side (e.g., adverse) effects.

Most controlled-release formulations are designed to initially release an amount of drug that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In another embodiment, the compositions of the present invention can be formulated as a water soluble gel. High concentrations of silicate or a compound of Formula I, such as a silicate or a compound of Formula I salt, are titrated back to neutrality, a gel is formed around pH 7.6. This gel is suitable for topical administration to an ulcer, such as a skin ulcer, and wounds in accordance with the present invention. An ulcer as described herein is a local defect of the surface of an organ or tissue, which is produced by the sloughing of inflammatory necrotic tissue.

The compositions of the present invention can also be prepared in combination with other active ingredients such that the composition comprises silicate or a compound of Formula I as the first active ingredient, and one or more other active ingredients.

For example, the use of an adjuvant is well known to enhance a normal immune response to circumstances such as vaccination. Many adjuvants slow the release of antigen into the body and thereby forming a reservoir of antigen which gradually releases and so provides a prolonged antigenic stimulus. For example, antigens that normally persist for only a few days may be retained in the body for several weeks by means of adjuvants. Thus, the immune response to an antigen present within a vaccine may be increased by including an adjuvant and an effective amount of a silicate or a compound of Formula I containing composition of the present invention.

Accordingly, in another embodiment, the compositions of the present invention can comprise an antigen, an adjuvant effective to enhance an immune response, and a silicate or a compound of Formula I. It is believed that inclusion of a silicate or a compound of Formula I within an antigen and an adjuvant will bring about beneficial improvements in the macrophage population, specifically with respect to antigen presenting cells such as macrophages.

A "purified" silicate or a compound of Formula I, including a silicate or a compound of Formula I salt, as described herein refers to substantially pure silicate or a compound of Formula I, which is substantially free, essentially free, or free of another compound. The purity of the silicate or a compound of Formula I refers to the silicate or a compound of Formula I prior to its formulation in a pharmaceutical composition.

In one embodiment, the silicate or compound of Formula I in the pharmaceutical composition preferably has a molecular weight less than 1000 daltons and more preferably, less than 500 daltons.

In yet another embodiment, the silicate or a compound of Formula I of the present invention can be run through activated charcoal. For example, a silicate or a compound of Formula I solution can be run through an activated charcoal filter at the end of a syringe prior to administration.

Therapeutic Methods

As used herein, the terms "treat", "treating" and "treatment" refer to the eradication or amelioration of a disease or symptoms associated with a disease. In certain embodiments, such terms refer to minimizing the spread or worsening of the disease resulting from the administration of one or more therapeutic agents to a patient with such a disease.

As used herein, the terms "prevent", "preventing" and "prevention" refer to the prevention of the onset, recurrence or spread of the disease in a patient resulting from the administration of a therapeutic agent.

The term "effective amount" as used herein refers to an amount of silicate or a compound of Formula I sufficient to provide a therapeutic or prophylactic benefit in the treatment or prevention of a disease or to delay or minimize symptoms associated with a disease. Further, a therapeutically effective amount with respect to a silicate or a compound of Formula I means that amount of therapeutic agent alone, or in combination with other therapies, that provides a therapeutic benefit in the treatment or prevention of a disease. Used in connection with a silicate or a compound of Formula I, the term can encompass an amount that improves overall therapy, reduces or avoids symptoms or causes of disease, or enhances the therapeutic efficacy of or synergizes with another therapeutic agent.

The compositions of the present invention are suitable for preventing or treating (including alleviating the severity of) a number of disease and disorders in a patient. The present invention is suitable for treating many conditions because it is believed to stimulate the innate immune system and therefore, a macrophages inflammatory response.

A "patient" includes an animal (e.g., cow, horse, sheep, pig, chicken, turkey, quail, cat, dog, mouse, rat, rabbit or guinea pig), in one embodiment a mammal such as a non-primate and a primate (e.g., monkey and human), and in another embodiment a human. In a preferred embodiment, a patient is a human. In specific embodiments, the patient is a human infant, child, adolescent or adult.

For example, silicate or a compound of Formula I can be used to treat abscesses, bacterial infections including methicillin resistant bacterial infections, *Clostridium difficile* infections, *Clostridium. perfringens*, and Enterococcal infections, inflammatory conditions such as dermatitis, osteoarthritis, rheumatoid arthritis, psoriatic arthritis, Crohn's disease, systemic lupus erythematosus, peritonitis, sepsis, endotoxic shock, adult respiratory distress syndrome, chronic obstructive pulmonary disease, allograft rejection, asthma, graft-versus-host-disease, congestive heart failure and cystic fibrosis and psoriasis, cancer including a solid tumor such as a melanoma and carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, neuroblastomas, and the like, diseases from various viruses, including influenza, respiratory syncytial virus, HIV, papilloma virus, hepatitis B virus, hepatitis C virus and herpes, and spinal cord injury, and promoting bone growth and repair Additionally, diseases involving the gastrointestinal tract and associated tissues (such as appendicitis, peptic, gastric and duodenal ulcers, peritonitis, pancreatitis, ulcerative colitis, pseudomembranous, acute and ischemic colitis, diverticulitis, epiglottitis, achalasia, cholangitis, coeliac disease, cholecystitis, hepatitis, enteritis, and Whipple's disease); systemic or local inflammatory diseases and conditions (such as allergy, anaphylactic shock, immune complex disease, organ ischemia, reperfusion injury, organ necrosis, hay fever, septicemia, cachexia, hyperpyrexia, eosinophilic granuloma, granulomatosis, and sarcoidosis); diseases involving the urogential system and associated tissues (such as septic abortion, epididymitis, vaginitis, prostatitis and urethritis); diseases involving the respiratory system and associated tissues (such as bronchitis, emphysema, rhinitis, cystic fibrosis, adult respiratory distress syndrome, pneumonitis, pneumoultramicroscopicsilicovolcanoconiosis, alvealitis, bronchiolitis, pharyngitis, pleurisy, and sinusitis); diseases arising from infection by bacteria (such as disseminated bacteremia, Dengue fever), fungi (such as candidiasis) and protozoal and multicellular parasites (such as malaria, filariasis, amebiasis, and hydatid cysts); dermatological diseases and conditions of the skin (such as burns, dermatitis, dermatomyositis, sunburn, urticaria warts, and wheals); diseases involving the cardiovascular system and associated tissues (such as vasulitis, angiitis, endocarditis, arteritis, atherosclerosis, thrombophlebitis, pericarditis, myocarditis, myocardial ischemia, congestive heart failure, periarteritis *nodosa*, and rheumatic fever); diseases involving the central or peripheral nervous system and associated tissues (such as Alzheimer's disease, meningitis, encephalitis, multiple sclerosis, cerebral infarction, cerebral embolism, Guillame-Barre syndrome, neuritis, neuralgia, spinal cord injury, paralysis, and uveitis); diseases of the bones, joints, muscles and connective tissues (such as the various arthritides and arthralgias, osteomyelitis, fasciitis, Paget's disease, gout, periodontal disease, rheumatoid arthritis, and synovitis); other autoimmune and inflammatory disorders (such as myasthenia gravis, thryoiditis, systemic lupus erythematosus, Goodpasture's syndrome, Behcets's syndrome, allograft rejection, graft-versus-host disease, ankylosing spondylitis, Berger's disease, Type I diabetes, ankylosing spondylitis, Berger's disease, and Retier's syndrome); as well as various cancers, tumors and proliferative disorders are also contemplated for treatment by the present invention.

The silicate containing compositions or the compounds of Formula I of the present invention are not toxic to all cells alike but appear to be cytotoxic to cells that are "stressed" (e.g., virally infected cells, tumor cells, etc.).

The present invention is also suitable for promoting tissue remodeling and for treating or preventing infections resulting from an invasive procedure, such as the insertion of foreign objects into a body including needles, catheters, scalpel blades, fiberoptic devices, laparoscopic surgical tools and accessories, biopsy needles, intravenous catheters, shunts, dental tools, dental floss, and similar devices and invasive techniques. In all the aforementioned cases, the foreign material which is transiently introduced into the body and/or through tissues of the body may be treated with an effective amount of a silicate or a compound of Formula I present on the surface of the foreign material and/or applied to the affected tissues during or subsequent to the procedure.

Furthermore, in another embodiment, the compositions of the present invention are also suitable for reducing scar tissue formation. A major clinical problem relating to surgical repair is adhesion which occurs during the initial phases of the healing process after surgery or disease. The most common form of adhesion occurs after surgery as a result of trauma, although adhesion may occur as a result of other processes or events such as pelvic inflammatory disease, mechanical injury, radiation treatment and the presence of foreign material. The silicate or a compound of Formula I containing compositions of the present invention, however, are suitable for limiting tissue apposition, thereby minimizing scar formation. Likewise, the silicate or a compound of Formula I containing compositions of the present invention are also suitable for reducing scar tissue formation in a burn victim, or a scar from an internal wound or an internal surgical scar.

In yet another embodiment, the silicate or a compound of Formula I compositions of the present invention are suitable for treating a number of syndromes associated with an impaired chemotaxis of neutrophils such as complement deficiencies, antibody deficiencies, Wiscott-Aldrich syndrome, chronic mucocutaneous candidiasis, Chediak-Higashi syndrome, hyperimmunoglobulin E syndrome, chronic granulomatous disease, and diabetes mellitus. Deficiencies in neutrophil chemotaxis are attributable either to defects in the production of chemotacetic factors, for example C5a, or to an intrinsic defect in the neutrophils themselves. Numerous deficiencies involving neutrophil chemotaxis are associated with neutrophils which are poorly mobilized and defective in random motility. A common clinical symptom of neutrophil dysfunction includes recurrent skin abscesses. Applicants believe that topical application of an effective amount of a silicate or a compound of Formula I can increase the number of neutrophils in the affected area and bring about clinical improvement in the skin abscesses.

Other neutrophil dysfunction syndromes are characterized by neutrophils which are metabolically defective and hence have a lower efficiency. Thus, increasing the number of neutrophils present by application of, or introduction of, an effective amount of a silicate or a compound of Formula I composition of the present invention can bring about therapeutic benefits by concentrating the number of available neutrophils. Even where the overall population of neutrophils may have reduced activity, increasing the total number of functioning neutrophils in a localized area will treat the disorder.

In another embodiment, a silicate or a compound of Formula I containing composition may be employed for administration in combination with other therapeutic agents, such as a chemotherapeutic agent, antibiotic, or other agent used to treat a given condition, either consecutively, simultaneously, or sequentially.

Also contemplated in the present invention is the use of the compositions of the present invention for cosmetic and dermatological purposes. For example, the compositions of the present invention can be used to combat the visual signs of aging. Aging causes modifications of the skin's structure and its cutaneous function and the main clinical signs of aging are, among others, the appearance of fine wrinkles and deep wrinkles that increase with age.

In yet another embodiment, the compositions of the present invention can be used to treat bacterial infections that cause pharyngitis (sore throat) by, for example, gargling with the compositions of the present invention. The clinical symptoms of pharyngitis is dry scratchiness and painful swallowing that results from an inflammation of the pharynx.

Similarly, the compositions of the present invention can be used to treat the "common cold" or alleviate "common cold" symptoms caused by a virus such as rhinovirus.

Also provided in the present invention is a method for treating citrus canker by, for example, delivering the composition of the present invention to trees. Citrus canker is a bacterial disease that afflicts citrus trees that causes premature leaf and fruit drop. Citrus canker is highly contagious and can be spread rapidly by windborne rain, lawnmowers and other landscaping equipment, people carrying the infection on their hands, clothing, or equipment and moving infected or exposed plants or plant parts.

The following non-limiting examples are given by way of illustration only and are not to be considered limitations of this invention. There are many apparent variations within the scope of this invention.

Example 1: Metastatic Models

Melanoma Model

One million B16 melanoma cells were intravenously administered to 3 mice (experimental group), and 600,000 B16 cells were given to a control group of 3 mice. 3 days later 3 mice were treated with 100 µg sodium silicate in PBS (intravenously), 135 µg sodium silicate in water (intraperitoneally) and 135 µg sodium silicate in water (intraperitoneally) on days 4, 5 and 6 post B16 cell IV administration, respectively. An exemplary treated mouse from the experimental group is shown in FIGS. 1C & D and did not have evidence of tumors in the peritoneal cavity. Conversely, the untreated mice contained more than 60 tumors in the peritoneal cavity (62, 64 and 71 tumors on each of the three mice). See FIGS. 1A & B.

Sarcoma Model

Two million S180 cells were intraperitoneally injected into 8 mice. 3 days later, 100 µg, 50 µg, and 50 µg sodium silicate in sterile water was then administered subcutaneously to 4 mice on days 4, 5 and 6 post IP injection of S180 cells, respectively. At day 14 post S180 cell administration, all four untreated control mice showed extensive ascites and by day 23, all died. The 4 treated mice, however, showed no signs of ascites and remain healthy beyond 45 days.

Example 2: Subcutaneous Melanoma Model

Figure 2:
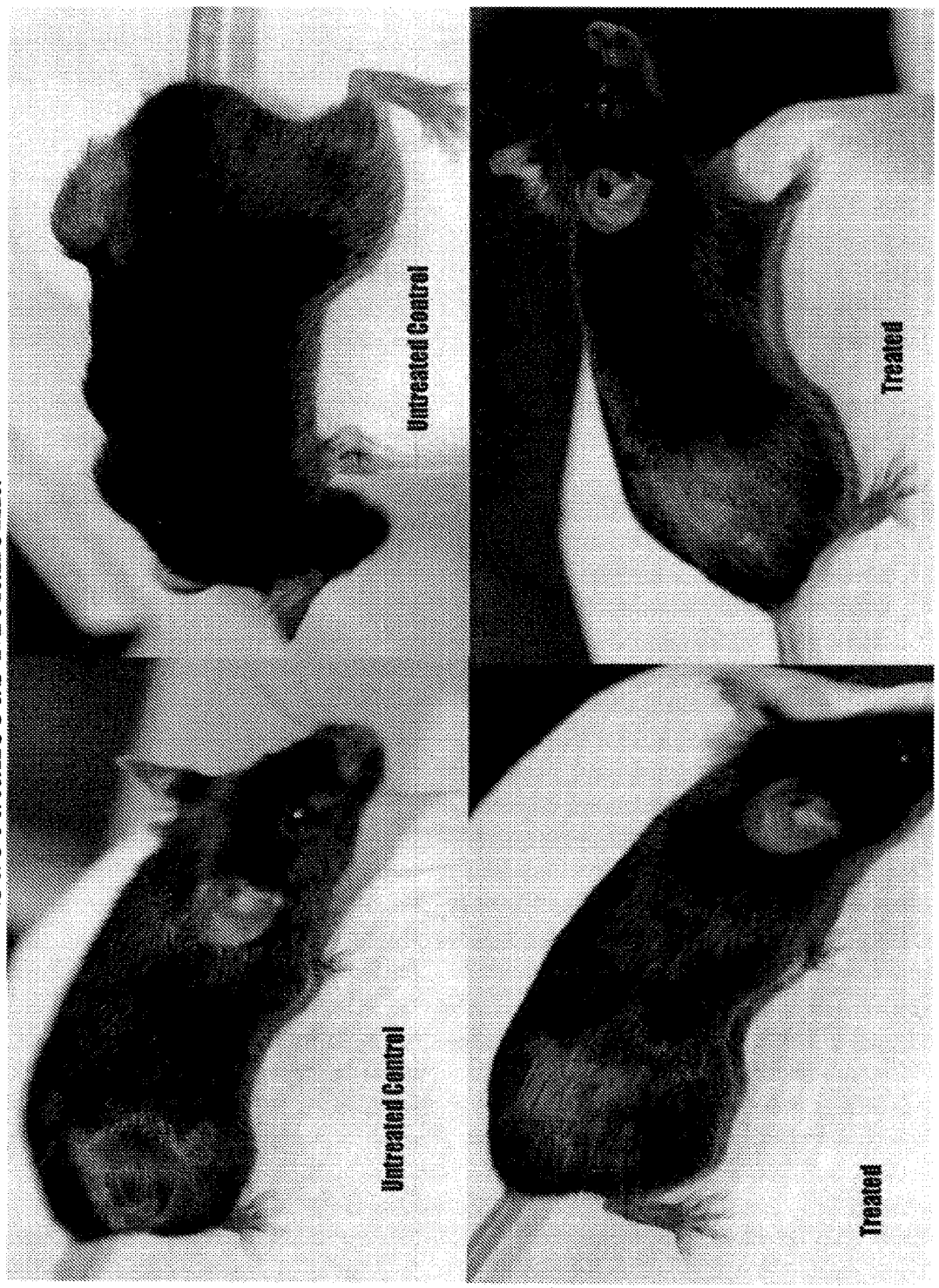
FIG. 2. Photograph of untreated (top panel) and treated (bottom panel) mice containing B16 melanoma cells. Treated mice were administered 100 μg, 50 μg, and 50 μg sodium silicate in sterile water subcutaneously for three consecutive days, respectively, following administration of S180 cells.

One million B16 melanoma cells were injected subcutaneously into four mice, two in experimental group, two in treatment group. Three days later, 135 µg sodium silicate was injected subcutaneously into the same site of the mouse in the treatment group for three consecutive days. Following B16 melanoma cell administration, control group received PBS only. FIG. 2 demonstrates that 2 weeks following initial injection of tumor cells, the treated mouse had no visible signs of a tumor (FIG. 2 bottom panel), while the untreated mouse had a visible tumor (FIG. 2, top panel).

Example 3: Sodium Silicate Activates Leukocytes

Figure 3:
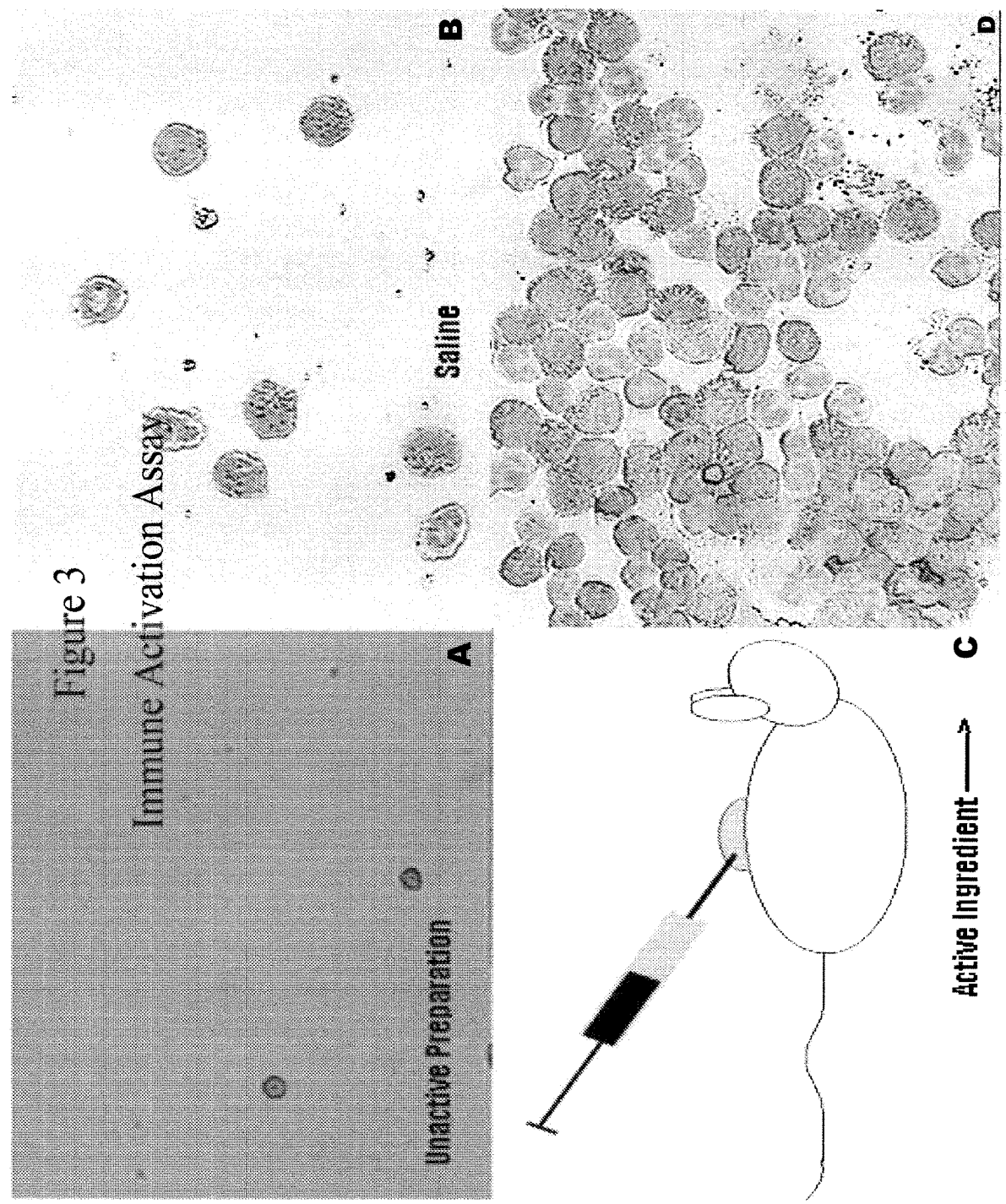
FIG. 3. Light micrograph of cells flushed from mice locally treated with PBS (A), saline (B), or sodium silicate (D). Results demonstrate leukocyte infiltration.

Normal, healthy mice were injected with air to create an air pocket under the skin. Thereafter, the air "bubble" was injected with either 0.5 ml of PBS alone (FIG. 3A), 0.5 ml saline solution (FIG. 3B), or 1.35 mg/ml sodium silicate in water (FIG. 3C). 19 hours later, the pocket was flushed with PBS, spun down onto a slide, and dried and stained with Wright stain. Upon examination with a light microscope, mice treated with sodium silicate have a large number of leukocytes in the visual field, compared to mice treated with PBS or saline.

Figure 4:
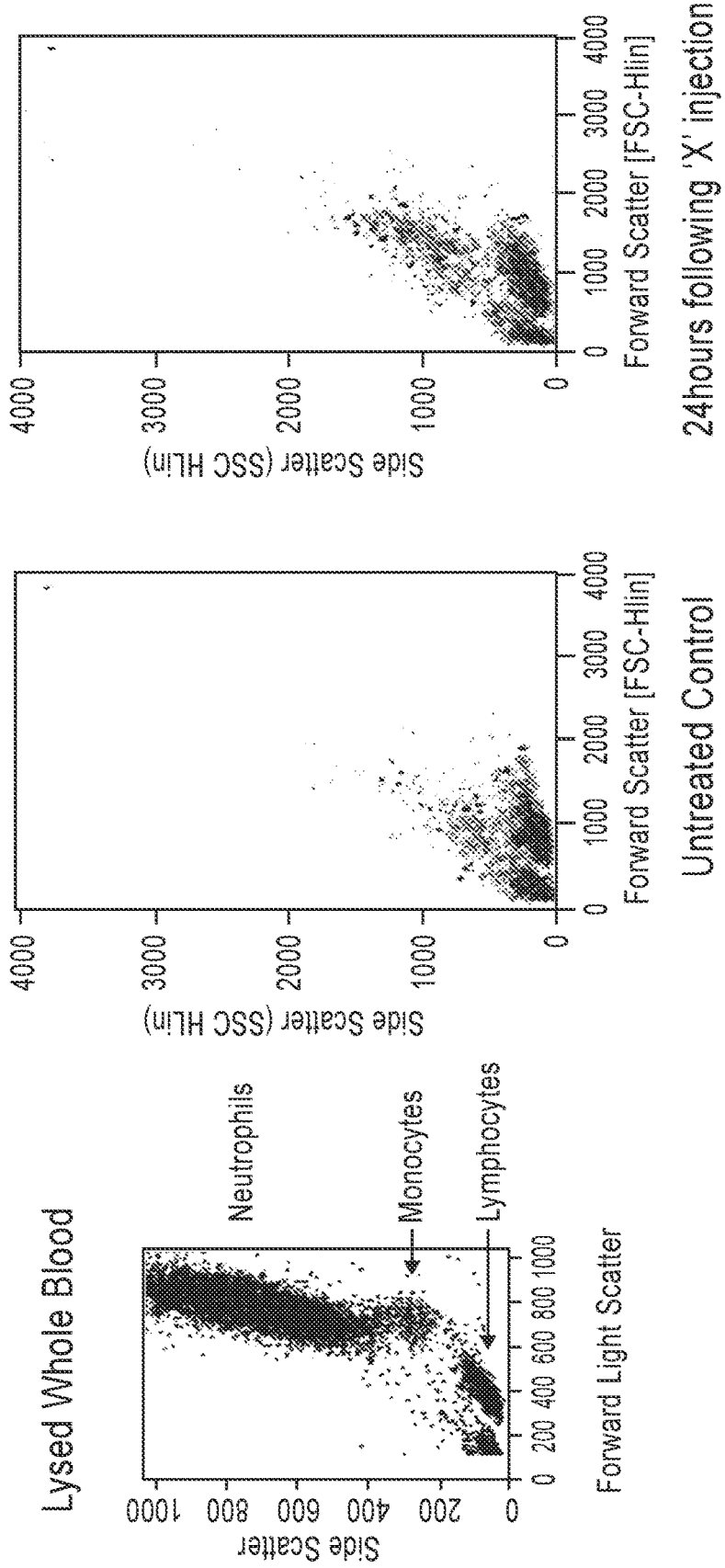
FIG. 4. Flow cytometer light scatter experiment of cells from mice treated with sodium silicate.

In a separate experiment, two mice were injected with 20 µg sodium silicate to produce a blood concentration of 10 µg/ml. 20 hours later, mice were bled, red blood cells were lysed, and all other cells were put in a flow cytometer. Two control mice received PBS. Light scatter experiment demonstrated that mostly leukocytes were present upon administration of sodium silicate (FIG. 4).

Additionally, three mice were injected with sodium silicate as described above and bled. Cells were lysed and stained with Mac-1 (Becton Dickinson). Mac-1 stains for both granulocytes and monocytes. Flow cytometry analysis demonstrates that cells receiving sodium silicate contained approximately 140% more cells (approximately a 1.5 fold increase) that stained for Mac 1 than control mice that received PBS (data not shown). Three control mice were given PBS.

Example 4. Sodium Silicate Aids in Tissue Remodeling

Horse suffering from trauma to right leg was administered sodium silicate prepared by taking 1 gram of a solution containing 27% by weight $Na_2SiO_3$ and 14% by weight NaOH and diluting it to 200 ml in distilled water. HCl was added to neutralize the solution to pH 7.6.

The sodium silicate solution was administered in an atomizer one time per day, for approximately one week. Although hair at site of injury historically comes in white, possibly due to local inflammation and damage to hair follicles, the hair at the site of injury grew in the with natural hair color of horse, which was indistinguishable in color from hair adjacent to wound. These data demonstrate that sodium silicate has an effect on tissue remodelling and repair.

Example 5: Wound Healing

Figure 5:
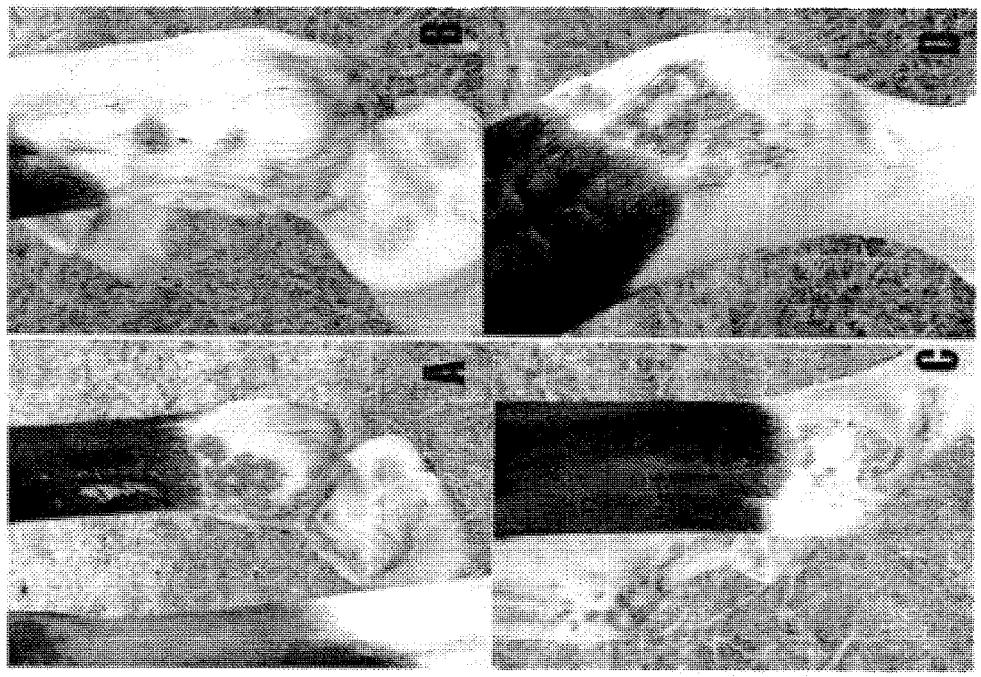
FIG. 5. Photograph of the left and right hind legs of a horse containing wounds.

Horse containing a wound on inside and outside of right and left hind legs (FIG. 5) was treated with sodium silicate prepared by taking 1 gram of a solution containing 27% by weight $Na_2SiO_3$ and 14% by weight NaOH and diluting it to 200 ml in distilled water. HCl was added to neutralize the solution to pH 7.6.

Figure 6:
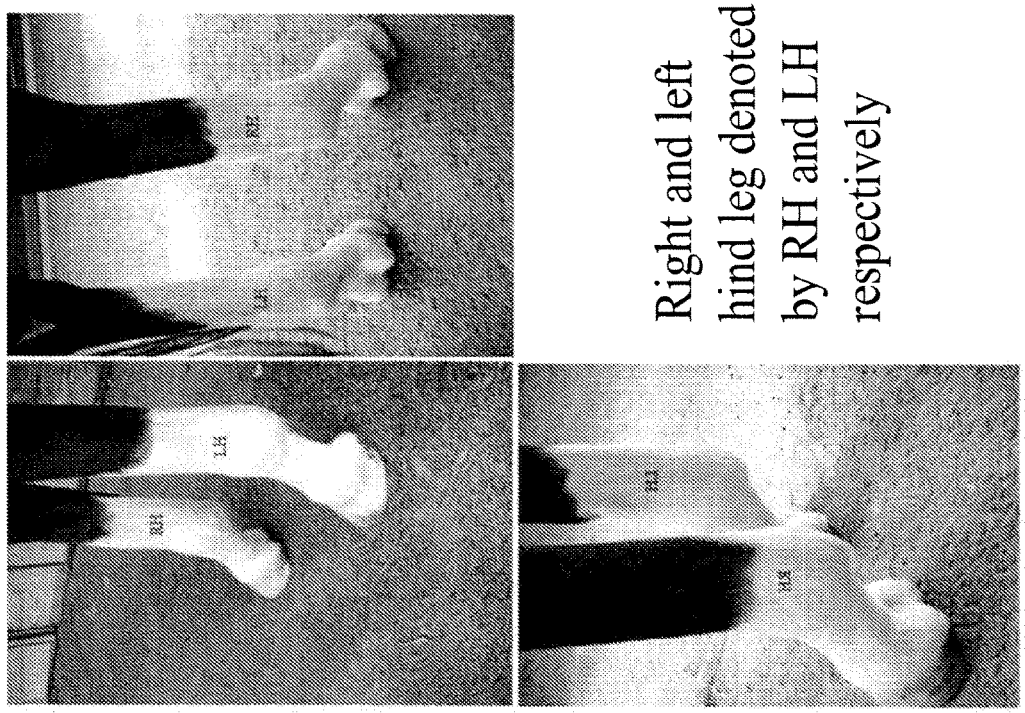
FIG. 6. Photograph of the left and right hind legs of a horse two weeks following treatment with 5 mg/ml sodium silicate.
Figure 7:
FIG. 7. Photograph of the left and right hind legs of a horse containing wounds not receiving treatment.

The sodium silicate solution was administered in an atomizer to the lower portion of each hind leg one time per day, for two consecutive days. FIG. 6 demonstrates that two weeks after treatment, the wounds on the right and left hind legs of the horse are completely cleared, while the untreated horse (FIG. 7) contains an apparent wounds on the right hind leg that appears to have gotten worse during the two week experimental period.

Example 6: Coated Sutures

A filtered, sterilized solution of an effective amount of sodium silicate, potassium silicate, or other silicate, is applied to suture threads. The application of the silicate solution to the sutures is made immediately prior to the suture's use in surgery but the sutures can be obtained pre-coated or pre-impregnated with an effective amount of the silicate material. The presence of the silicate on the suture material will promote healing of the tissue being sutured, have a beneficial effect on possible infections that occur along the tissues being sutured, and bring about other noted improvements associated with a stimulated neutrophil and macrophage population which occurs in response to the presence of the metal silicate.

Example 7: Cutaneous Wound

Patient with a cutaneous wound that cuts through the epidermis and full dermis thickness is treated with a topical application of sodium silicate. Sodium silicate enhances the neutrophil and macrophage response and persistence within the scar tissue and therefore, allows the scar tissue to bear a closer physical appearance and function compared to the surrounding non-scarred tissue.

Example 8: Toxicity of Sodium Silicate on 3T3 and L-929 Cells in Culture

3T3 and L-929 cells were separately grown in the absence (FIG. 8A) and presence (FIG. 8B) of serum. As provided in FIG. 8, varying amounts of sodium silicate per ml PBS were added to the culture after cells were grown to about 30-50% confluency. Growth stimulation is depicted below the X axis and cytotoxicity is demonstrated above the X axis. Data demonstrates that tumor cells (L-929) are killed at concentrations above 10 µg/ml of sodium silicate, while growth of non-tumor cells (3T3) is supported and even slightly stimulated through higher concentrations of sodium silicate, and not killed until at least 100 µg/ml sodium silicate. The cells are being killed by necrosis. Thus, sodium silicate is not toxic to all tumor and non-tumor cells alike but appears to be specific for tumor cells.

Embodiments

1. A method of treating an inflammatory condition, autoimmune disease, a bacterial or viral infection, or cancer comprising administering a composition that comprises a silicate as the active ingredient.

2. The method of embodiment 1, wherein the composition comprises a silicate salt.

3. The method of embodiment 2, wherein the composition comprises a sodium, potassium, or lithium silicate salt.

4. The method of embodiment 1, wherein the composition consists essentially of a silicate salt.

5. The method of embodiment 1, wherein the composition is administered topically, intravenously or subcutaneously.

6. The method of embodiment 1, wherein the cancer is a solid tumor.

7. The method of embodiment 6, wherein the cancer is selected from the group consisting of a melanoma, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinoma, adenocarcinoma, small cell carcinoma, glioma, and neuroblastoma.

8. The method of embodiment 1, wherein the bacterial or viral infection is a *Staphylococcus* infection, *Streptococcus* infection, influenza, respiratory syncytial virus, HIV, hepatitis B virus, hepatitis C virus, papilloma virus and herpes.

9. The method of embodiment 1, wherein the inflammatory condition or autoimmune disease is osteoarthritis, psoriatic arthritis, Crohn's disease, inflammatory diseases or disorders include, without limitation, asthma, lung inflammation, chronic granulomatous diseases such as tuberculosis, leprosy, sarcoidosis, and silicosis, nephritis, amyloidosis, rheumatoid arthritis, ankylosing spondylitis, chronic bronchitis, scleroderma, lupus, polymyositis, appendicitis, inflammatory bowel disease, ulcers, Sjorgen's syndrome, Reiter's syndrome, psoriasis, pelvic inflammatory disease, orbital inflammatory disease, thrombotic disease, and inappropriate allergic responses to environmental stimuli such as poison ivy, pollen, insect stings and certain foods, including atopic dermatitis and contact dermatitis.

10. A method for healing an infected or uninfected wound comprising administering a composition comprising administering a silicate as the active ingredient.

11. The method of embodiment 10, wherein the wound is a skin ulcer, such as a decubitus ulcer, diabetic skin ulcer, burn ulcer, traumatic ulcer, crural ulcer, diabetic gangrene, or a surgical site wound.

12. A method for inducing an anti-inflammatory response comprising administering a composition that comprises a silicate as the active ingredient.

13. A method for activating monocytic cell in vivo, comprising administering a composition that comprises a silicate as the active ingredient.

14. A pharmaceutical composition consisting essentially of

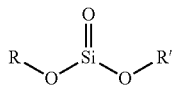

and a pharmaceutically acceptable excipient, wherein R and R' are independently selected from the group consisting of hydrogen, a monovalent cation, a divalent cation, a quaternary ammonium, and an organic fragment.

15. The pharmaceutical composition of embodiment 14, wherein R and R' are independently selected from the group consisting of a sodium or potassium ion.

16. A pharmaceutical composition comprising a silicate, wherein the composition comprises at least 0.1% w/v silicate.

17. The pharmaceutical composition of embodiment 16, wherein the composition is not a red oak bark extract.

18. A pharmaceutical composition that liberates a silicate anion in vivo, wherein the silicate anion is the active ingredient.

19. The pharmaceutical composition of claim 18, wherein the composition comprises at least 0.1% w/v silicate.

20. A pharmaceutical composition consisting essentially of Formula I and a pharmaceutically acceptable excipient, wherein R and R' are independently selected from the group consisting of hydrogen, a monovalent cation, a divalent cation, a quaternary ammonium, and an organic fragment.

21. A method of treating an inflammatory condition, autoimmune disease, a bacterial or viral infection, or cancer comprising administering a composition that comprises Formula I as the active ingredient.

22. A method for activating monocytic cell in vivo, comprising administering a composition that comprises a Formula I as the active ingredient.

23. A pharmaceutical composition comprising Formula I, wherein the composition comprises at least 0.1% w/v Formula I.

The invention claimed is:

1. A method of treating or ameliorating a viral infection, comprising administering to a subject in need of treatment or amelioration a composition comprising a solution with an active agent, wherein the active agent consists essentially of a silicate that liberates orthosilicic acid in vivo, and the solution has a pH of about 6.5-7.8; and the active agent is present at a concentration of about 1-5 mg/mL.

2. The method of claim 1, wherein the composition is administered parenterally, orally, topically, intravenously or subcutaneously.

3. The method of claim 1, wherein the aqueous solution has a pH of 7.6.

4. The method of claim 1, wherein the active agent is present at a concentration of about 5 mg/mL.

5. The method of claim 1, wherein the active agent is present at a concentration of about 1-3 mg/mL.

6. The method of claim 1, wherein the active agent is present at a concentration of about 1-2 mg/mL.

7. The method of claim 1, wherein said administering is oral or intravenous.

8. The method of claim 1, wherein said administering is topical.

9. The method of claim 1, wherein the active agent is silicic acid.

10. The method of claim 1, wherein the viral infection is one or more of influenza, respiratory syncytial virus, HIV, papilloma virus, hepatitis B virus, hepatitis C virus, or herpes.

11. The method of claim 1, wherein the viral infection is caused by rhinovirus.

12. A method of treating or ameliorating a viral infection, comprising administering to a subject in need of treatment or amelioration a composition, wherein the composition is prepared by a method consisting essentially of forming an aqueous solution of an orthosilicic acid salt and adjusting the pH of said solution to about 6.0-8.0, wherein said administering is by injection.

13. The method of claim 12, wherein the viral infection is one or more of influenza, respiratory syncytial virus, HIV, papilloma virus, hepatitis B virus, hepatitis C virus, or herpes.

14. The method of claim 12, wherein the viral infection is caused by rhinovirus.

15. The method of claim 12, wherein the solution has a pH of about 6.5-7.8.

16. The method of claim 12, wherein the aqueous solution has a pH of 7.6.

17. The method of claim 12, wherein the orthosilicic acid salt is present at a concentration of about 5 mg/mL.

18. The method of claim 12, wherein the orthosilicic acid salt is present at a concentration of about 1-3 mg/mL.

19. The method of claim 12, wherein the orthosilicic acid salt is present at a concentration of about 1-2 mg/mL.

* * * * *